United States Patent
Dutreix et al.

(10) Patent No.: US 9,205,101 B2
(45) Date of Patent: Dec. 8, 2015

(54) CANCER TREATMENT BY COMBINING DNA MOLECULES MIMICKING DOUBLE STRAND BREAKS WITH HYPERTHERMIA

(75) Inventors: Marie Dutreix, L'Hay-les-Roses (FR); Jian-Sheng Sun, Saint Maur des Fosses (FR); Flavien Devun, Orsay (FR)

(73) Assignees: INSTITUT CURIE, Paris Cedex (FR); DNA THERAPEUTICS, Evry Cedex (FR)

( * ) Notice: Subject to any disclaimer, the term of this patent is extended or adjusted under 35 U.S.C. 154(b) by 0 days.

(21) Appl. No.: 14/118,583

(22) PCT Filed: May 25, 2012

(86) PCT No.: PCT/EP2012/059799
§ 371 (c)(1),
(2), (4) Date: Nov. 19, 2013

(87) PCT Pub. No.: WO2012/163814
PCT Pub. Date: Dec. 6, 2012

(65) Prior Publication Data
US 2014/0100266 A1   Apr. 10, 2014

(30) Foreign Application Priority Data
May 27, 2011   (EP) .................................... 11305650

(51) Int. Cl.
| | |
|---|---|
| *C12N 15/11* | (2006.01) |
| *A61K 31/713* | (2006.01) |
| *A61K 31/00* | (2006.01) |
| *C12N 15/113* | (2010.01) |
| *C12N 15/115* | (2010.01) |

(52) U.S. Cl.
CPC ............... *A61K 31/713* (2013.01); *A61K 31/00* (2013.01); *C12N 15/11* (2013.01); *C12N 15/113* (2013.01); *C12N 15/115* (2013.01); *C12N 2310/13* (2013.01); *C12N 2310/315* (2013.01); *C12N 2310/3183* (2013.01); *C12N 2310/3515* (2013.01); *C12N 2310/53* (2013.01)

(58) Field of Classification Search
None
See application file for complete search history.

(56) References Cited

U.S. PATENT DOCUMENTS 6,420,176 B1 * 7/2002 Lisziewicz et al. ........... 435/455
7,635,722 B1 * 12/2009 Bachynsky et al. ........... 514/728

FOREIGN PATENT DOCUMENTS

| WO | WO 2008/034866 | | 3/2008 |
| WO | WO 2010056403 | A1 * | 5/2010 |
| WO | WO 2010/082821 | | 7/2010 |
| WO | WO 2011161075 | A1 * | 12/2011 |

OTHER PUBLICATIONS

Storm et al, Hyperthermic Therapy for Human Neoplasms: Thermal Death Time, 2006, Cancer, vol. 46, 8: 1849-1854.*
Solass, W. et al. "Therapeutic approach of human peritoneal carcinomatosis with Dbait in combination with capnoperitoneum: proof of concept" *Surgical Endoscopy*, 2012, pp. 847-852, vol. 26.
Quanz, M. et al. "Small-Molecule Drugs Mimicking DNA Damage: A New Strategy for Sensitizing Tumors to Radiotherapy" *Clinical Cancer Research*, 2009, pp. 1308-1316, vol. 15.
Written Opinion in International Application No. PCT/EP2012/059799, Sep. 12, 2012, pp. 1-7.
Devun, F. et al. "Preclinical study of the DNA repair inhibitor Dbait in combination with chemotherapy in colorectal cancer" *Journal of Gastroenterology*, 2012, pp. 266-275, vol. 47.
Quanz, M. et al, "Hyperactivation of DNA-PK by Double-Strand Break Mimicking Molecules Disorganizes DNA Damage Response" *PloS ONE*, Jul. 2009, pp. 1-11, vol. 4, Issue 7.

* cited by examiner

*Primary Examiner* — Tracy Vivlemore
*Assistant Examiner* — Kate Poliakova
(74) *Attorney, Agent, or Firm* — Saliwanchik, Lloyd & Eisenschenk

(57) ABSTRACT

The present invention relates to a method for treating a cancer including a combination of a treatment by a nucleic acid molecule mimicking double strand breaks with hyperthermia.

20 Claims, 2 Drawing Sheets

SEQUENCE LISTING

<160> NUMBER OF SEQ ID NOS: 37

<210> SEQ ID NO 1
<211> LENGTH: 32
<212> TYPE: DNA
<213> ORGANISM: artificial sequence
<220> FEATURE:
<223> OTHER INFORMATION: Dbait32

<400> SEQUENCE: 1
acgcacgggt gttgggtcgt tgttcggat ct                                      32

<210> SEQ ID NO 2
<211> LENGTH: 32
<212> TYPE: DNA
<213> ORGANISM: artificial sequence
<220> FEATURE:
<223> OTHER INFORMATION: Dbait32Ha

<400> SEQUENCE: 2
cgtaggtctg tttggtggct ttgcagtggc ac                                     32

<210> SEQ ID NO 3
<211> LENGTH: 32
<212> TYPE: DNA
<213> ORGANISM: artificial sequence
<220> FEATURE:
<223> OTHER INFORMATION: Dbait32Hb

<400> SEQUENCE: 3
gctaggcttg tttgctgggt tgtaggcaca gc                                     32

<210> SEQ ID NO 4
<211> LENGTH: 32
<212> TYPE: DNA
<213> ORGANISM: artificial sequence
<220> FEATURE:
<223> OTHER INFORMATION: Dbait32Hc

<400> SEQUENCE: 4
gctgtgccca caccccagca aacaagccta ga                                     32

<210> SEQ ID NO 5
<211> LENGTH: 32
<212> TYPE: DNA
<213> ORGANISM: artificial sequence
<220> FEATURE:
<223> OTHER INFORMATION: Dbait32Hd

<400> SEQUENCE: 5
gctaggtctg tttggtggct ttgcagtggc ac                                     32

<210> SEQ ID NO 6
<211> LENGTH: 32
<212> TYPE: DNA
<213> ORGANISM: artificial sequence
<220> FEATURE:
<223> OTHER INFORMATION: nucleic acid molecule Ia
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or proteins

<400> SEQUENCE: 6
acgcacgggt gttgggtcgt ttgttcggat ct                                       32

<210> SEQ ID NO 7
<211> LENGTH: 32
<212> TYPE: DNA
<213> ORGANISM: artificial sequence
<220> FEATURE:
<223> OTHER INFORMATION: nucleic acid molecule Ib
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or proteins

<400> SEQUENCE: 7
cgtaggtctg tttggtggct ttgcagtggc ac                                       32

<210> SEQ ID NO 8
<211> LENGTH: 32
<212> TYPE: DNA
<213> ORGANISM: artificial sequence
<220> FEATURE:
<223> OTHER INFORMATION: nucleic acid molecule Ic
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or proteins

<400> SEQUENCE: 8
gctaggcttg tttgctgggt tgtaggcaca gc                                       32

<210> SEQ ID NO 9
<211> LENGTH: 32
<212> TYPE: DNA
<213> ORGANISM: artificial sequence
<220> FEATURE:
<223> OTHER INFORMATION: nucleic acid molecule Id
<220> FEATURE:

```
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or proteins

<400> SEQUENCE: 9
gctgtgccca aacccagca aacaagccta ga                                    32

<210> SEQ ID NO 10
<211> LENGTH: 32
<212> TYPE: DNA
<213> ORGANISM: artificial sequence
<220> FEATURE:
<223> OTHER INFORMATION: nucleic acid molecule Ie
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or proteins

<400> SEQUENCE: 10
gctaggtctg tttggtggct ttgcagtggc ac                                   32

<210> SEQ ID NO 11
<211> LENGTH: 32
<212> TYPE: DNA
<213> ORGANISM: artificial sequence
<220> FEATURE:
<223> OTHER INFORMATION: nucleic acid molecule IIa
<220> FEATURE:
<221> NAME/KEY: misc_feature
<223> OTHER INFORMATION: note="at the 3' end of the complementary strand
      the three last nucleotides with phosphorothioate or
``` methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
        backbone
<220> FEATURE:
<221> NAME/KEY: stem_loop
<222> LOCATION: (1)..(32)
<220> FEATURE:
<221> NAME/KEY: misc_feature
<222> LOCATION: (1)..(1)
<223> OTHER INFORMATION: at the 5' end, Lm = carboxamido oligoethylene
        glycol + C = single or double chain fatty acids, cholesterol,
        sugars, peptides or proteins
<220> FEATURE:
<221> NAME/KEY: misc_feature
<222> LOCATION: (32)..(32)
<223> OTHER INFORMATION: loop L' =hexaethyleneglycol,
        tetradeoxythymidylate or 2,19-bis(phosphor)-8-hydraza-1-hydroxy-4-
        oxa-9-oxo-nonadecane

<400> SEQUENCE: 11
acgcacgggt gttgggtcgt tgttcggat ct                                      32

<210> SEQ ID NO 12
<211> LENGTH: 32
<212> TYPE: DNA
<213> ORGANISM: artificial sequence
<220> FEATURE:
<223> OTHER INFORMATION: nucleic acid molecule IIb
<220> FEATURE:
<221> NAME/KEY: misc_feature
<223> OTHER INFORMATION: note="at the 3' end of the complementary strand
        the three last nucleotides with phosphorothioate or
        methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
        backbone
<220> FEATURE:
<221> NAME/KEY: stem_loop
<222> LOCATION: (1)..(32)
<220> FEATURE:
<221> NAME/KEY: misc_feature
<222> LOCATION: (1)..(1)
<223> OTHER INFORMATION: at the 5' end, Lm = carboxamido oligoethylene
        glycol + C = single or double chain fatty acids, cholesterol,
        sugars, peptides or proteins
<220> FEATURE:
<221> NAME/KEY: misc_feature
<222> LOCATION: (32)..(32)
<223> OTHER INFORMATION: loop L' =hexaethyleneglycol,
        tetradeoxythymidylate or 2,19-bis(phosphor)-8-hydraza-1-hydroxy-4-
        oxa-9-oxo-nonadecane

<400> SEQUENCE: 12
cgtaggtctg tttggtggct ttgcagtggc ac                                     32

<210> SEQ ID NO 13
<211> LENGTH: 32
<212> TYPE: DNA
<213> ORGANISM: artificial sequence
<220> FEATURE:
<223> OTHER INFORMATION: nucleic acid molecule IIc
<220> FEATURE:
<221> NAME/KEY: misc_feature
<223> OTHER INFORMATION: note="at the 3' end of the complementary strand
        the three last nucleotides with phosphorothioate or
        methylphosphonate backbone"
<220> FEATURE:
<221> NAME/KEY: modified_base
<222> LOCATION: (1)..(3)
<223> OTHER INFORMATION: mod_base= phosphorothioate or methylphosphonate

```
        backbone
<220> FEATURE:
<221> NAME/KEY: stem_loop
<222> LOCATION: (1)..(32)
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 13
gctaggcttg tttgctgggt tgtaggcaca gc                                    32

<210> SEQ ID NO 14
<211> LENGTH: 32
<212> TYPE: DNA
<213> ORGANISM: artificial sequence
<220> FEATURE:
<223> OTHER INFORMATION: nucleic acid molecule IId
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 14
gctgtgccca aacccagca aacaagccta ga                                     32

<210> SEQ ID NO 15
<211> LENGTH: 32
<212> TYPE: DNA
<213> ORGANISM: artificial sequence
<220> FEATURE:
<223> OTHER INFORMATION: nucleic acid molecule IIe
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
```

```
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 15
gctaggtctg tttggtggct ttgcagtggc ac                                    32

<210> SEQ ID NO 16
<211> LENGTH: 32
<212> TYPE: DNA
<213> ORGANISM: artificial sequence
<220> FEATURE:
<223> OTHER INFORMATION: nucleic acid molecule IIIa
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note= "the last nucleotide at the 3' end of the
      complementary strand is linked to Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 16
acgcacgggt gttgggtcgt tgttcggat ct                                     32

<210> SEQ ID NO 17
<211> LENGTH: 32
<212> TYPE: DNA
<213> ORGANISM: artificial sequence
<220> FEATURE:
<223> OTHER INFORMATION: nucleic acid molecule IIIb
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note= "the last nucleotide at the 3' end of the
      complementary strand is linked to Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
```

-continued

```
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 17
cgtaggtctg tttggtggct ttgcagtggc ac                                      32

<210> SEQ ID NO 18
<211> LENGTH: 32
<212> TYPE: DNA
<213> ORGANISM: artificial sequence
<220> FEATURE:
<223> OTHER INFORMATION: nucleic acid molecule IIIc
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note= "the last nucleotide at the 3' end of the
      complementary strand is linked to Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 18
gctaggcttg tttgctgggt tgtaggcaca gc                                      32

<210> SEQ ID NO 19
<211> LENGTH: 32
<212> TYPE: DNA
<213> ORGANISM: artificial sequence
<220> FEATURE:
<223> OTHER INFORMATION: nucleic acid molecule IIId
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note= "the last nucleotide at the 3' end of the
      complementary strand is linked to Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
```

-continued oxa-9-oxo-nonadecane

<400> SEQUENCE: 19
gctgtgccca acccagca aacaagccta ga     32

<210> SEQ ID NO 20
<211> LENGTH: 32
<212> TYPE: DNA
<213> ORGANISM: artificial sequence
<220> FEATURE:
<223> OTHER INFORMATION: nucleic acid molecule IIIe
<220> FEATURE:
<221> NAME/KEY: misc_feature
<223> OTHER INFORMATION: note="at the 3' end of the complementary strand the three last nucleotides with phosphorothioate or methylphosphonate backbone"
<220> FEATURE:
<221> NAME/KEY: misc_feature
<223> OTHER INFORMATION: note= "the last nucleotide at the 3' end of the complementary strand is linked to Lm = carboxamido oligoethylene glycol + C = single or double chain fatty acids, cholesterol, sugars, peptides or proteins
<220> FEATURE:
<221> NAME/KEY: modified_base
<222> LOCATION: (1)..(3)
<223> OTHER INFORMATION: mod_base= phosphorothioate or methylphosphonate backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol, tetradeoxythymidylate or 2,19-bis(phosphor)-8-hydraza-1-hydroxy-4-oxa-9-oxo-nonadecane

<400> SEQUENCE: 20
gctaggtctg tttggtggct ttgcagtggc ac     32

<210> SEQ ID NO 21
<211> LENGTH: 32
<212> TYPE: DNA
<213> ORGANISM: artificial sequence
<220> FEATURE:
<223> OTHER INFORMATION: nucleic acid molecule DT01
<220> FEATURE:
<221> NAME/KEY: misc_feature
<223> OTHER INFORMATION: note="at the 3' end of the complementary strand the three last nucleotides with phosphorothioate backbone"
<220> FEATURE:
<221> NAME/KEY: misc_feature
<222> LOCATION: (1)..(1)
<223> OTHER INFORMATION: at the 5' end, 10-O-[1-propyl-3-N-carbamoylcholesteryl]-triethyleneglycol radical
<220> FEATURE:
<221> NAME/KEY: modified_base
<222> LOCATION: (1)..(3)
<223> OTHER INFORMATION: mod_base= phosphorothioate  backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' = 2,19-bis(phosphor)-8-hydraza-1-hydroxy-4-oxa-9-oxo-nonadecane

<400> SEQUENCE: 21
gctgtgccca acccagca aacaagccta ga     32

<210> SEQ ID NO 22
<211> LENGTH: 32

-continued

```
<212> TYPE: DNA
<213> ORGANISM: artificial sequence
<220> FEATURE:
<223> OTHER INFORMATION: nucleic acid molecule Ia
<220> FEATURE:
<221> NAME/KEY: modified_base
<222> LOCATION: (30)..(32)
<223> OTHER INFORMATION: phosphorothioate or methylphosphonate backbone

<400> SEQUENCE: 22
agatccgaac aaacgaccca acaccgtgc gt                                      32

<210> SEQ ID NO 23
<211> LENGTH: 32
<212> TYPE: DNA
<213> ORGANISM: artificial sequence
<220> FEATURE:
<223> OTHER INFORMATION: nucleic acid molecule IIa
<220> FEATURE:
<221> NAME/KEY: modified_base
<222> LOCATION: (30)..(32)
<223> OTHER INFORMATION: phosphorothioate or methylphosphonate backbone

<400> SEQUENCE: 23
agatccgaac aaacgaccca acaccgtgc gt                                      32

<210> SEQ ID NO 24
<211> LENGTH: 32
<212> TYPE: DNA
<213> ORGANISM: artificial sequence
<220> FEATURE:
<223> OTHER INFORMATION: nucleic acid molecule IIIa
<220> FEATURE:
<221> NAME/KEY: modified_base
<222> LOCATION: (30)..(32)
<223> OTHER INFORMATION: phosphorothioate or methylphosphonate backbone

<400> SEQUENCE: 24
agatccgaac aaacgaccca acaccgtgc gt                                      32

<210> SEQ ID NO 25
<211> LENGTH: 32
<212> TYPE: DNA
<213> ORGANISM: artificial sequence
<220> FEATURE:
<223> OTHER INFORMATION: nucleic acid molecule Ib
<220> FEATURE:
<221> NAME/KEY: modified_base
<222> LOCATION: (30)..(32)
<223> OTHER INFORMATION: phosphorothioate or methylphosphonate backbone

<400> SEQUENCE: 25
gtgccactgc aaagccacca aacagaccta cg                                     32

<210> SEQ ID NO 26
<211> LENGTH: 32
<212> TYPE: DNA
<213> ORGANISM: artificial sequence
<220> FEATURE:
<223> OTHER INFORMATION: nucleic acid molecule IIb
<220> FEATURE:
<221> NAME/KEY: modified_base
<222> LOCATION: (30)..(32)
<223> OTHER INFORMATION: phosphorothioate or methylphosphonate backbone

<400> SEQUENCE: 26
gtgccactgc aaagccacca aacagaccta cg                                     32

<210> SEQ ID NO 27
```

-continued

```
<211> LENGTH: 32
<212> TYPE: DNA
<213> ORGANISM: artificial sequence
<220> FEATURE:
<223> OTHER INFORMATION: nucleic acid molecule IIIb
<220> FEATURE:
<221> NAME/KEY: modified_base
<222> LOCATION: (30)..(32)
<223> OTHER INFORMATION: phosphorothioate or methylphosphonate backbone

<400> SEQUENCE: 27
gtgccactgc aaagccacca aacagaccta cg                                    32

<210> SEQ ID NO 28
<211> LENGTH: 32
<212> TYPE: DNA
<213> ORGANISM: artificial sequence
<220> FEATURE:
<223> OTHER INFORMATION: nucleic acid molecule Ic
<220> FEATURE:
<221> NAME/KEY: modified_base
<222> LOCATION: (30)..(32)
<223> OTHER INFORMATION: phosphorothioate or methylphosphonate backbone

<400> SEQUENCE: 28
gctgtgccta caacccagca aacaagccta gc                                    32

<210> SEQ ID NO 29
<211> LENGTH: 32
<212> TYPE: DNA
<213> ORGANISM: artificial sequence
<220> FEATURE:
<223> OTHER INFORMATION: nucleic acid molecule IIc
<220> FEATURE:
<221> NAME/KEY: modified_base
<222> LOCATION: (30)..(32)
<223> OTHER INFORMATION: phosphorothioate or methylphosphonate backbone

<400> SEQUENCE: 29
gctgtgccta caacccagca aacaagccta gc                                    32

<210> SEQ ID NO 30
<211> LENGTH: 32
<212> TYPE: DNA
<213> ORGANISM: artificial sequence
<220> FEATURE:
<223> OTHER INFORMATION: nucleic acid molecule IIIc
<220> FEATURE:
<221> NAME/KEY: modified_base
<222> LOCATION: (30)..(32)
<223> OTHER INFORMATION: phosphorothioate or methylphosphonate backbone

<400> SEQUENCE: 30
gctgtgccta caacccagca aacaagccta gc                                    32

<210> SEQ ID NO 31
<211> LENGTH: 32
<212> TYPE: DNA
<213> ORGANISM: artificial sequence
<220> FEATURE:
<223> OTHER INFORMATION: nucleic acid molecule Id
<220> FEATURE:
<221> NAME/KEY: modified_base
<222> LOCATION: (30)..(32)
<223> OTHER INFORMATION: phosphorothioate or methylphosphonate backbone

<400> SEQUENCE: 31
tctaggcttg tttgctgggt tgtgggcaca gc                                    32
```

```
<210> SEQ ID NO 32
<211> LENGTH: 32
<212> TYPE: DNA
<213> ORGANISM: artificial sequence
<220> FEATURE:
<223> OTHER INFORMATION: nucleic acid molecule IId
<220> FEATURE:
<221> NAME/KEY: modified_base
<222> LOCATION: (30)..(32)
<223> OTHER INFORMATION: phosphorothioate or methylphosphonate backbone

<400> SEQUENCE: 32
tctaggcttg tttgctgggt tgtgggcaca gc                                    32

<210> SEQ ID NO 33
<211> LENGTH: 32
<212> TYPE: DNA
<213> ORGANISM: artificial sequence
<220> FEATURE:
<223> OTHER INFORMATION: nucleic acid molecule IIId
<220> FEATURE:
<221> NAME/KEY: modified_base
<222> LOCATION: (30)..(32)
<223> OTHER INFORMATION: phosphorothioate or methylphosphonate backbone

<400> SEQUENCE: 33
tctaggcttg tttgctgggt tgtgggcaca gc                                    32

<210> SEQ ID NO 34
<211> LENGTH: 32
<212> TYPE: DNA
<213> ORGANISM: artificial sequence
<220> FEATURE:
<223> OTHER INFORMATION: nucleic acid molecule Ie
<220> FEATURE:
<221> NAME/KEY: modified_base
<222> LOCATION: (30)..(32)
<223> OTHER INFORMATION: phosphorothioate or methylphosphonate backbone

<400> SEQUENCE: 34
gtgccactgc aaagccacca aacagaccta gc                                    32

<210> SEQ ID NO 35
<211> LENGTH: 32
<212> TYPE: DNA
<213> ORGANISM: artificial sequence
<220> FEATURE:
<223> OTHER INFORMATION: nucleic acid molecule IIe
<220> FEATURE:
<221> NAME/KEY: modified_base
<222> LOCATION: (30)..(32)
<223> OTHER INFORMATION: phosphorothioate or methylphosphonate backbone

<400> SEQUENCE: 35
gtgccactgc aaagccacca aacagaccta gc                                    32

<210> SEQ ID NO 36
<211> LENGTH: 32
<212> TYPE: DNA
<213> ORGANISM: artificial sequence
<220> FEATURE:
<223> OTHER INFORMATION: nucleic acid molecule IIIe
<220> FEATURE:
<221> NAME/KEY: modified_base
<222> LOCATION: (30)..(32)
<223> OTHER INFORMATION: phosphorothioate or methylphosphonate backbone

<400> SEQUENCE: 36
gtgccactgc aaagccacca aacagaccta gc                                    32
```

```
<210> SEQ ID NO 37
<211> LENGTH: 32
<212> TYPE: DNA
<213> ORGANISM: artificial sequence
<220> FEATURE:
<223> OTHER INFORMATION: nucleic acid molecule DT01 (from SEQ 21) or
      Dbait32Hc (from SEQ 4)
<220> FEATURE:
<221> NAME/KEY: modified_base
<222> LOCATION: (30)..(32)
<223> OTHER INFORMATION: phosphorothioate or methylphosphonate backbone

<400> SEQUENCE: 37
tctaggcttg tttgctgggt tgtgggcaca gc                                     32
```

CANCER TREATMENT BY COMBINING DNA MOLECULES MIMICKING DOUBLE STRAND BREAKS WITH HYPERTHERMIA

CROSS-REFERENCE TO RELATED APPLICATION

This application is the U.S. national stage application of International Patent Application No. PCT/EP2012/059799, filed May 25, 2012.

The Sequence Listing for this application is labeled "Seq-List-replace-2.txt" which was created on Jul. 10, 2015 and is 21 KB. The entire contents of the sequence listing is incorporated herein by reference in its entirety.

FIELD OF THE INVENTION

The invention relates to the field of oncology.

BACKGROUND OF THE INVENTION

Hyperthermia is one of the oldest clinically applied agents enhancing the effectiveness of various anti-cancer therapies. Hyperthermia is a type of treatment in which body tissue is exposed to high temperatures to damage and kill cancer cells or to make cancer cells more sensitive to the effects of radiation and certain anticancer drugs (cyclophosphamide, doxorubicin, cisplatin, etoposide, ifosfamide, gemcitabine, interferon-alpha, vincristine, carboplatin, oxaliplatin . . . ). It is generally not used alone. The studies have focused on the treatment of many types of cancer, including sarcoma, melanoma, head and neck, brain, lung, esophagus, breast, bladder, rectum, liver, cervix and peritoneal mesothelium. However, the exact mode of action of hyperthermia remains elusive.

WO 2010/082821 and Krawczyk et al (2011, Proc Natl Acad Sci) disclose that mild hyperthermia inhibits homologous recombination (HR) and induces BRCA2 degradation. Homologous recombination is one of pathways to repair of double-stranded break (DSB). It is known that BRCA2 is involved in recombinational repair of double-stranded break (DSB) and that PARP inhibitors are effective in killing BRCA2-defective breast cancer cells. Therefore, the authors postulated that an agent inducing DSBs may be used for treating cancer while simultaneously inhibited BRCA2 (and then homologous recombination) by hyperthermia. They also suggested further using a PARP inhibitor with this combination. PARP is involved in the detection and signaling single strand DNA breaks (SSB) to the enzymatic machinery involved in the SSB repair. These authors finally observed that the increase of sensitivity to radiotherapy by hyperthermia is specific of homologous recombination since this effect was not observed in cells deficient for homologous recombination (Rad54−/−).

Even if cancer treatment with hyperthermia is progressing, there is still a strong need for improved methods of cancer treatments using hyperthermia.

SUMMARY OF THE INVENTION

The inventors surprisingly discovered that, contrary to what has been shown by Krawczyk et al and what is known about DNA dependent protein kinase (DNA-PK), the effect of hyperthermia is not specific of homologous recombination pathway of DBS repair. More particularly, nucleic acid molecules mimicking double strand breaks, called Dbait molecules, may be useful for treating cancer in combination with hyperthermia. Dbait molecules act by hyperactivation of DNA dependent protein kinase (DNA-PK), involved the Non Homologous End Joining pathway of DNA double-strand break (DSB) repair without causing any additional DNA damages in cells (WO2005/040378; WO2008/034866; Quanz et al, 2009, *Clinical Cancer Research* 15:1308; Quanz et al, 2009, PLoS ONE 4:e6298; Dutreix et al, 2010, *Mut. Res.* 704:182). Surprisingly, inhibition of DNA repair by DNA-PK inhibitor NU7026 does not sensitize to hyperthermia and prevents Dbait sensitization. Therefore, Dbait sensitization requires DNA-PK kinase activation and acts independently of DSB DNA repair inhibition. They also showed that, surprisingly, the antitumoral effect of the combination of Dbait molecules with hyperthermia can be observed, even in absence of any agent inducing DSBs. In addition, the observed effect of the combination seems to be a synergistic and Dbait dose-dependent effect.

Therefore, the present invention concerns a nucleic acid molecule having at least one free end and a DNA double stranded portion of 24-200 bp with less than 60% sequence identity to any gene in a human genome for use for treating cancer in combination with hyperthermia treatment.

More preferably, the nucleic acid molecule has one of the following formulae:

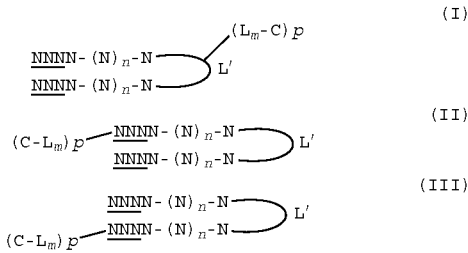

wherein N is a deoxynucleotide, n is an integer from 15 to 195, the underlined N refers to a nucleotide having or not a modified phosphodiester backbone, L' is a linker, C is a molecule facilitating endocytosis preferably selected from a lipophilic molecule and a ligand which targets cell receptor enabling receptor mediated endocytosis, L is a linker, m and p, independently, are an integer being 0 or 1.

More specifically, the nucleic acid molecule has one of the following formulae:

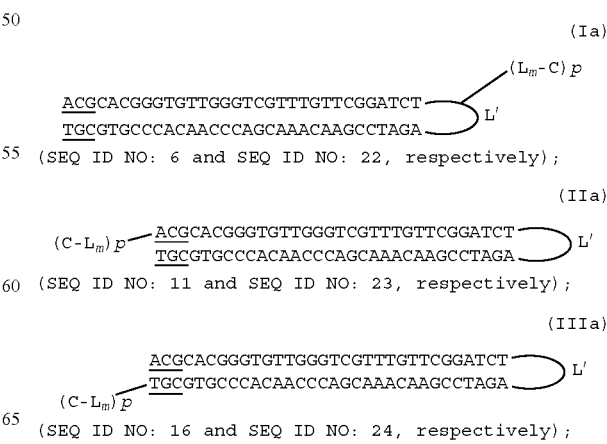

-continued (Ib)

```
      CGTAGGTCTGTTTGGTGGCTTTGCAGTGGCAC ─┐ (Lm-C)p
      GCATCCAGACAAACCACCGAAACGTCACCGTG ─┘ L'
```
(SEQ ID NO: 7 and SEQ ID NO: 25, respectively);

(IIb)

```
(C-Lm)p ─ CGTAGGTCTGTTTGGTGGCTTTGCAGTGGCAC ─┐ L'
          GCATCCAGACAAACCACCGAAACGTCACCGTG ─┘
```
(SEQ ID NO: 12 and SEQ ID NO: 26, respectively);

(IIIb)

```
          CGTAGGTCTGTTTGGTGGCTTTGCAGTGGCAC ─┐ L'
(C-Lm)p ─ GCATCCAGACAAACCACCGAAACGTCACCGTG ─┘
```
(SEQ ID NO: 17 and SEQ ID NO: 27, respectively);

(Ic)

```
      GCTAGGCTTGTTTGCTGGGTTGTAGGCACAGC ─┐ (Lm-C)p
      CGATCCGAACAAACGACCCAACATCCGTGTCG ─┘ L'
```
(SEQ ID NO: 8 and SEQ ID NO: 28, respectively);

(IIc)

```
(C-Lm)p ─ GCTAGGCTTGTTTGCTGGGTTGTAGGCACAGC ─┐ L'
          CGATCCGAACAAACGACCCAACATCCGTGTCG ─┘
```
(SEQ ID NO: 13 and SEQ ID NO: 29, respectively);

(IIIc)

```
          GCTAGGCTTGTTTGCTGGGTTGTAGGCACAGC ─┐ L'
(C-Lm)p ─ CGATCCGAACAAACGACCCAACATCCGTGTCG ─┘
```
(SEQ ID NO: 18 and SEQ ID NO: 30, respectively);

(Id)

```
      GCTGTGCCCACAACCCAGCAAACAAGCCTAGA ─┐ (Lm-C)p
      CGACACGGGTGTTGGGTCGTTTGTTCGGATCT ─┘ L'
```
(SEQ ID NO: 9 and SEQ ID NO: 31, respectively);

(IId)

```
(C-Lm)p ─ GCTGTGCCCACAACCCAGCAAACAAGCCTAGA ─┐ L'
          CGACACGGGTGTTGGGTCGTTTGTTCGGATCT ─┘
```
(SEQ ID NO: 14 and SEQ ID NO: 32, respectively);

(IIId)

```
          GCTGTGCCCACAACCCAGCAAACAAGCCTAGA ─┐ L'
(C-Lm)p ─ CGACACGGGTGTTGGGTCGTTTGTTCGGATCT ─┘
```
(SEQ ID NO: 19 and SEQ ID NO: 33, respectively);

(Ie)

```
      GCTAGGTCTGTTTGGTGGCTTTGCAGTGGCAC ─┐ (Lm-C)p
      CGATCCAGACAAACCACCGAAACGTCACCGTG ─┘ L'
```
(SEQ ID NO: 10 and SEQ ID NO: 34, respectively);

(IIe)

```
(C-Lm)p ─ GCTAGGTCTGTTTGGTGGCTTTGCAGTGGCAC ─┐ L'
          CGATCCAGACAAACCACCGAAACGTCACCGTG ─┘
```
(SEQ ID NO: 15 and SEQ ID NO: 35, respectively);

and, (IIIe)

```
          GCTAGGTCTGTTTGGTGGCTTTGCAGTGGCAC ─┐ L'
(C-Lm)p ─ CGATCCAGACAAACCACCGAAACGTCACCGTG ─┘
```
(SEQ ID NO: 20 and SEQ ID NO: 36, respectively);

wherein the underlined nucleotide refers to a nucleotide having a phosphorothioate or methylphosphonate backbone, the linked L' is selected from the group consisting of hexa-ethyleneglycol, tetradeoxythymidylate (T4) and 2,19-bis(phosphor)-8-hydraza-1-hydroxy-4-oxa-9-oxo-nonadecane; m is 1 and L is a carboxamido oligoethylene glycol, C is selected from the group consisting of single or double chain fatty acids such as octadecyl and dioleoyl, cholesterol, tocopherol, folic acid, sugar such as galactose and mannose and their oligosaccharide, peptide such as RGD and bombesin and protein such as integrin, preferably cholesterol.

In a preferred embodiment, the nucleic acid molecule is selected from the group consisting of (Id)

```
      GCTGTGCCCACAACCCAGCAAACAAGCCTAGA ─┐ (Lm-C)p
      CGACACGGGTGTTGGGTCGTTTGTTCGGATCT ─┘ L'
```

(IId)

```
(C-Lm)p ─ GCTGTGCCCACAACCCAGCAAACAAGCCTAGA ─┐ L',
          CGACACGGGTGTTGGGTCGTTTGTTCGGATCT ─┘
``` and (IIId)

```
          GCTGTGCCCACAACCCAGCAAACAAGCCTAGA ─┐ L'.
(C-Lm)p ─ CGACACGGGTGTTGGGTCGTTTGTTCGGATCT ─┘
```

In a very specific embodiment, the nucleic acid molecule is

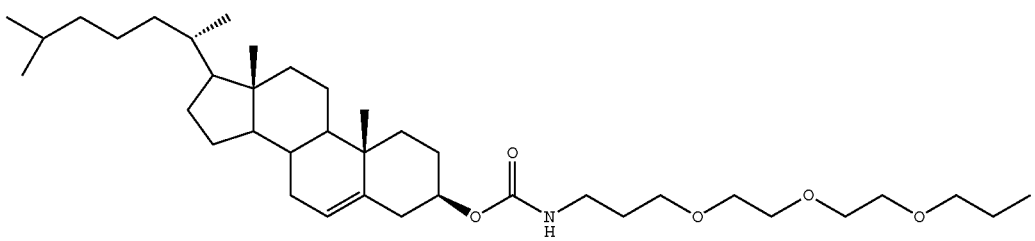

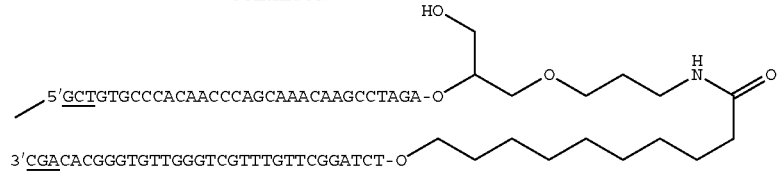

More preferably, the molecule facilitating endocytosis is cholesterol.

Preferably, the hyperthermia treatment involves a temperature of at least 41° C., preferably at least 42° C. Optionally, the hyperthermia treatment is performed by microwaves (RFA), ultrasound, infrared rays, nanoparticles or nanotubes, induction heating, magnetic hyperthermia, perfusion or infusion of pre-warmed liquid such as blood, intraperitoneal heated flow, drug-induced hyperthermia, or direct application of heat.

Preferably, the cancer is a solid cancer, preferably selected from be sarcoma, melanoma, and cancers of the head and neck, kidney, ovary, pancreas, prostate, thyroid, lung, esophagus, breast, bladder, colorectum, liver, cervix, and endometrial and peritoneal cancers, more preferably liver and peritoneal cancer.

In a particular embodiment, p is 1 (i.e., a conjugated Dbait molecule) and the nucleic acid molecule is used in combination with an endomosolytic agent, preferably a quinoline endomosolytic agent, more preferably chloroquine or hydroxychloroquine. Still more preferably, the nucleic acid molecule is used in combination with chloroquine.

Optionally, the nucleic acid molecule may be used in combination with a radiotherapy, a radioisotope therapy and/or an antitumoral chemotherapy. Preferably, the antitumoral chemotherapy is a treatment by a DNA damaging antitumoral agent, either directly or indirectly. More preferably, the DNA damaging antitumoral agent is selected from the group consisting of an inhibitor of topoisomerases I or II, a DNA crosslinker, a DNA alkylating agent, an anti-metabolic agent and inhibitors of the mitotic spindles.

Alternatively, the nucleic acid molecule is not used in combination with a radiotherapy, a radioisotope therapy and/or an antitumoral chemotherapy. Preferably, the nucleic acid molecule is not used in combination with a radiotherapy, a radioisotope therapy and/or an antitumoral chemotherapy with a DNA damaging antitumoral agent.

MRC5 transformed fibroblasts and HT29 colon cancer cells were untreated or transfected with Dbait8H (1.25 mg/L) or Dbait32Hc (1.25 mg/L) in presence or absence of the DNA-PK inhibitor NU7026 (50 µM). After 5 hours, cells were submitted to hyperthermia at 43° C. during 1 hour. Cell mortality was measured by trypan blue assay 48 hours later. The mean percentage of cell death ± standard deviation from 5 independent experiments are represented. , $p<0.01$; *, $p<0.001$ with a Student t-test.

Figure 2A:
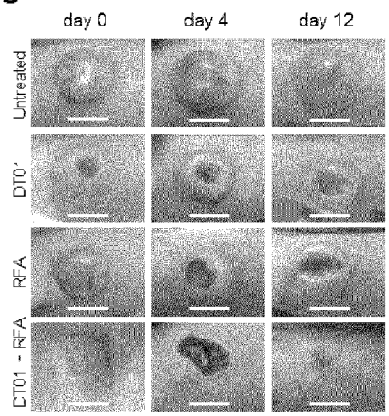
Figure 2B:
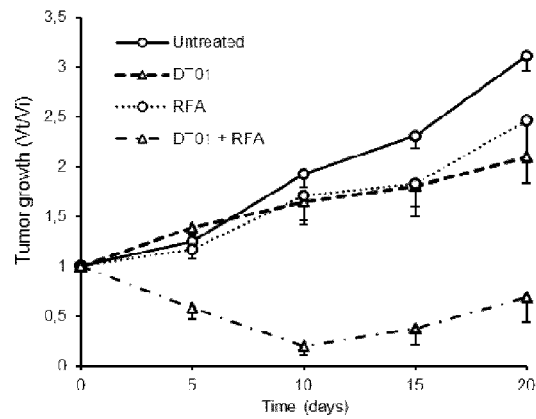

FIG. 2. DT01 enhances radiofrequency ablation antitumor effects.

Groups of NMR1 nude mice were implanted with $10^7$ tumor HT29 cells s.c. in the right flank. Mice were treated with RFA (2 minutes at 42° C. at the tumor periphery) (n=13), DT01 (4 local injections of 6 mg) (n=14), or both RFA and 4 injections of DT01 (n=11). Untreated tumor-bearing mice (n=11) served as controls. Panel A shows representative images of tumor aspect before treatment (day 0), then 4 and 12 day later (day 4 and day 12 respectively). Bar: 1 cm. Panel B shows the greater tumor growth suppression of mice treated with the combined treatment RFA+DT01. Mice were followed-up until sacrifice when tumors reached 2000 mm³. In all experiments, tumors were measured with a digital caliper 3 times a week. Tumor volumes were calculated in cubic millimeter using the following formula: length×width×width/2. Panel C shows the enhancement of survival of mice treated with the combined treatment RFA+DT01. Log rank test: Untreated vs RFA ($p<0.001$, RR 0.30); DT01+RFA vs RFA ($p<0.05$ RR 0.41).

Figure 3A:
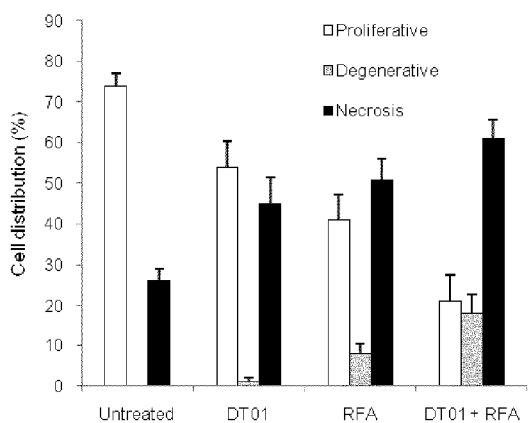
Figure 3B:
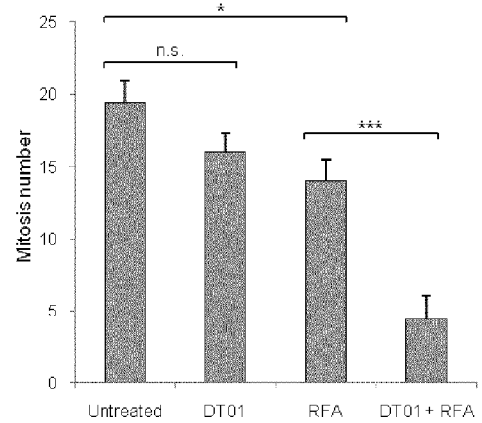

FIG. 3. Histologic analysis of treatment effects.

Groups of NMR1 nude mice (seven to eight mice per group) were implanted with $10^7$ tumor HT29 cells s.c. in the right flank. Mice were treated with RFA (2 minutes at 42° C. at the tumor periphery), DT01 (2 local injections of 6 mg), or both RFA and Dbait. Untreated tumor-bearing mice served as controls. Mice were euthanized 72 h after RFA treatment, and tumors excised for histological analysis. Panel A shows the cellular distribution of proliferative, degenerative and necrotic cells in the four experimental groups. Panel B shows the quantification of mitosis (mean value per tumor in 5 fields at magnification ×40) in the four experimental groups. Error bars indicate SEM (standard error of the mean). Specimens treated with RFA combined with DT01 showed significant larger areas of necrosis and degenerative cells, smaller areas of proliferative cells and lower number of mitosis compared with RFA alone or DT01 alone. Student t-test: *, $p<0.05$; ***, $p<0.001$.

Table 1. Survival and Pathological studies data.

Survival and pathological studies were performed as describe in materials and methods section. Complete responses consisted in total regression of the tumor 10 days after RFA treatment. Partial responses consisted in a 30% decrease, at least, of the longest tumor diameter. For pathological study, results are represented as mean±SD.

DETAILED DESCRIPTION OF THE INVENTION

The inventors surprisingly discovered that there is a high interest to use Dbait molecules for treating cancer in combination with hyperthermia. Indeed, these results are unexpected in respect of the suggested specificity of hyperthermia for homologous recombination pathway of DBS repair or of what is known for DNA-PK in the context of hyperthermia.

Indeed, in literature, the role of DNA-PK was investigated in radiosensitization (Zeng Z C et al. World J Gastroenterol 2002; 8:797-803; Woudstra E C et al. Radiat Res. 1999, 152:214-218; Dynlacht J R et al. J Cell Physiol. 2003, 196: 557-64.). The autors concluded that DNA-PKcs do not play any crucial role in the enhancement of cellular radiosensitivity by hyperthermia, and the radiosensitization by hyperthermia can be obtained irrespective of the Ku80 or DNA-PKcs status in cells. Therefore, they concluded that Ku80 or DNA- PKcs, and hence non homologous DSB end-joining, do not play any crucial role in the enhancement of cellular radiosensitivity by hyperthermia.

Figure 1:
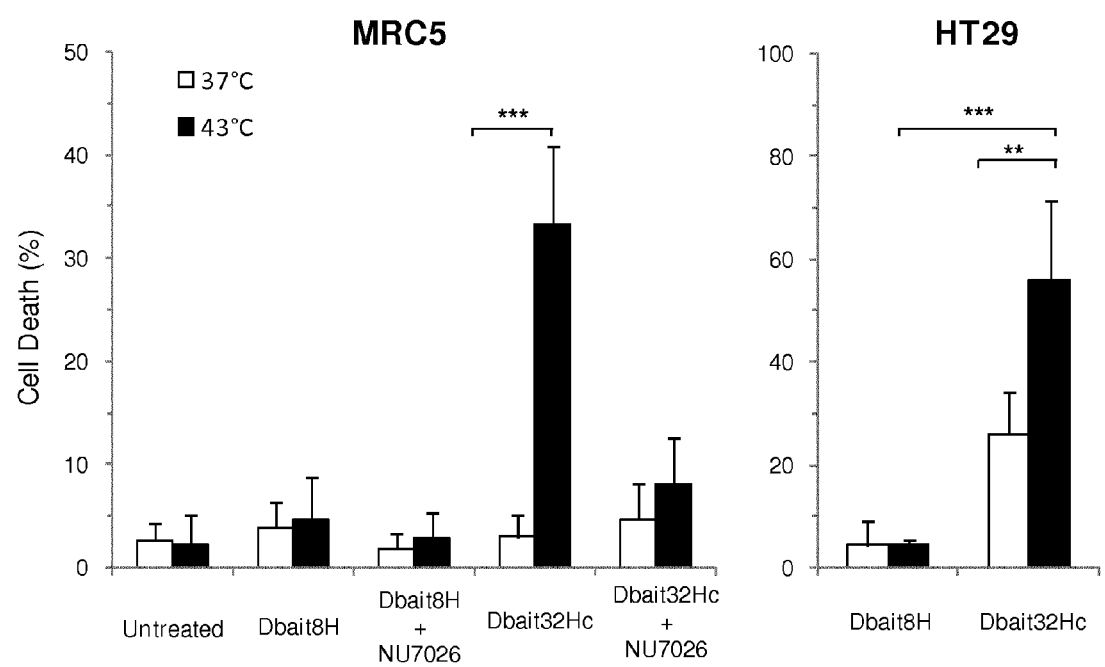
FIG. 1. Dbait32Hc induces synergic toxicity when associated with hyperthermia.
Figure 2C:
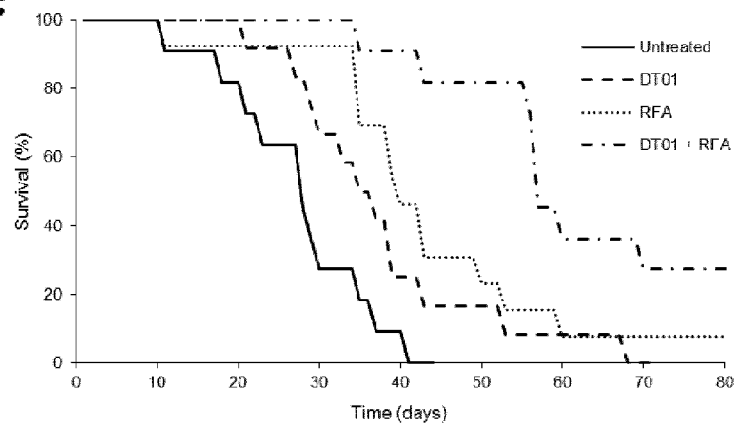

Inventors also showed that, surprisingly, the antitumoral effect of the combination of Dbait molecules and hyperthermia can be observed, even in absence of an agent inducing DSBs. More particularly, the inventors demonstrated, both in vitro and in vivo, that the combination of Dbait molecules with hyperthermia is of high interest for treating cancer. Indeed, a synergistic effect has been observed on the cancer cell death by combining Dbait molecules with hyperthermia. Classical inhibitors of DNA-PK kinase activity such as NU7026, that inhibit non homologous end joining repair (Veuger et al, 2004, Oncogene, 23, 7322-7329), do not induce hyperthermia sensitization (FIG. 1). The Dbait activity involved in hyperthermia sensitization strictly depends on DNA-PK kinase activity since it is abolished by NU7026. The hyperthermia and Dbait combined treatment allowed observing a drastic effect on the mice survival rate. Indeed, whereas there is less than 30% of survival with a treatment with hyperthermia or Dbait molecules alone at 50 days after treatment, the pool treated by the combination experienced 80% survival (FIG. 2C). Stabilization, or even a decrease, of the tumors size has been observed with the combination treatment. By analyzing the histology of excised tumors 3 days after treatments, the inventors observed that the tumors treated by the combination showed a highest destruction stage (degenerative and necrosis stages) than the tumor treated with hyperthermia or Dbait molecules alone (FIG. 3).

Based in these observations, the present invention relates to
- a pharmaceutical composition comprising a Dbait molecule or hairpin nucleic acid molecule as described below, optionally an anti-tumoral agent, preferably a DNA-damaging agent, and a pharmaceutically acceptable carrier, for use in the treatment of cancer in combination with hyperthermia;
- a pharmaceutical composition comprising a) a conjugated Dbait molecule or hairpin nucleic acid molecule as described below, b) an endosomolytic agent as described below, optionally c) an anti-tumoral agent, preferably a DNA-damaging agent, and d) a pharmaceutically acceptable carrier, for use in the treatment of cancer in combination with hyperthermia;
- a pharmaceutical composition comprising a Dbait molecule or hairpin nucleic acid molecule as described below, and a pharmaceutically acceptable carrier, for use in the treatment of cancer in combination with hyperthermia, but without any radiotherapy, any radioisotope therapy and any antitumoral chemotherapy, in particular any antitumoral chemotherapy with an agent inducing DBS;
- a pharmaceutical composition comprising a) a conjugated Dbait molecule or hairpin nucleic acid molecule as described below, b) an endosomolytic agent as described below, and c) a pharmaceutically acceptable carrier, for use in the treatment of cancer in combination with hyperthermia, but without any radiotherapy, any radioisotope therapy and any antitumoral chemotherapy, in particular any antitumoral chemotherapy with an agent inducing DBS;
- a product or kit containing a) a Dbait molecule or hairpin nucleic acid molecule as disclosed below, and optionally b) an anti-tumoral agent, preferably a DNA-damaging agent, as a combined preparation for simultaneous, separate or sequential use in the treatment of cancer in combination with hyperthermia, and optionally with radiotherapy or radioisotope therapy;
- a product or kit containing a) a conjugated Dbait molecule or hairpin nucleic acid molecule as disclosed below, b) an endosomolytic agent as described below, and optionally c) an anti-tumoral agent, preferably a DNA-damaging agent, as a combined preparation for simultaneous, separate or sequential use in the treatment of cancer in combination with hyperthermia, and optionally with radiotherapy or radioisotope therapy;
- a product or kit containing a) a conjugated Dbait molecule or hairpin nucleic acid molecule as disclosed below, and, b) an endosomolytic agent as described below, as a combined preparation for simultaneous, separate or sequential use in the treatment of cancer in combination with hyperthermia but without any radiotherapy, any radioisotope therapy and any antitumoral chemotherapy, in particular any antitumoral chemotherapy with an agent inducing DBS;
- a pharmaceutical composition comprising a Dbait molecule or hairpin nucleic acid molecule as disclosed below, for the use in the treatment of cancer in combination with hyperthermia and with a radiotherapy, a radioisotope therapy and/or a treatment with an antitumoral agent, preferably a DNA-damaging anti-tumoral agent;
- a pharmaceutical composition comprising a) a conjugated Dbait molecule or hairpin nucleic acid molecule as disclosed below, and b) an endosomolytic agent as described below, for the use in the treatment of cancer in combination with hyperthermia and with a radiotherapy, a radioisotope therapy and/or a treatment with a DNA-damaging anti-tumoral agent;
- the use of a pharmaceutical composition comprising a Dbait molecule or hairpin nucleic acid molecule as disclosed below for the manufacture of a medicament for the treatment of cancer in combination with hyperthermia; or for increasing the efficiency of the treatment of cancer with hyperthermia or for enhancing tumor sensitivity to hyperthermia;
- the use of a pharmaceutical composition comprising a Dbait molecule or hairpin nucleic acid molecule as disclosed below for the manufacture of a medicament for the treatment of cancer in combination with hyperthermia and with a radiotherapy, a radioisotope therapy and/or a treatment with an antitumoral agent, preferably a DNA-damaging anti-tumoral agent; or for increasing the efficiency of the treatment of cancer with hyperthermia and with a radiotherapy, a radioisotope therapy and/or a treatment with an antitumoral agent, preferably a DNA-damaging anti-tumoral agent; or for enhancing tumor sensitivity to hyperthermia and radiotherapy, radioisotope therapy and/or an antitumoral agent, preferably a DNA-damaging anti-tumoral agent;
- the use of a pharmaceutical composition comprising a Dbait molecule or hairpin nucleic acid molecule as disclosed below for the manufacture of a medicament for the treatment of cancer in combination with hyperthermia but without any radiotherapy, any radioisotope therapy and any antitumoral chemotherapy, in particular any antitumoral chemotherapy with an agent inducing DBS; or for increasing the efficiency of the treatment of cancer with hyperthermia without any radiotherapy, any radioisotope therapy and any antitumoral chemotherapy, in particular any antitumoral chemotherapy with an agent inducing DBS; or for enhancing tumor sensitivity to hyperthermia without any radiotherapy, any radioisotope therapy and any antitumoral chemotherapy, in particular any antitumoral chemotherapy with an agent inducing DBS;

the use of a pharmaceutical composition comprising a conjugated Dbait molecule or hairpin nucleic acid molecule as disclosed below for the manufacture of a medicament for the treatment of cancer in combination with hyperthermia and with a treatment with an endosomolytic agent as disclosed below;

the use of a pharmaceutical composition comprising a conjugated Dbait molecule or hairpin nucleic acid molecule as disclosed below for the manufacture of a medicament for the treatment of cancer in combination with hyperthermia and radiotherapy, radioisotope therapy and/or with an antitumoral agent, preferably a DNA-damaging anti-tumoral agent, and with an endosomolytic agent as disclosed below;

the use of a pharmaceutical composition comprising a conjugated Dbait molecule or hairpin nucleic acid molecule as disclosed below for the manufacture of a medicament for the treatment of cancer in combination with an endosomolytic agent as disclosed below and with hyperthermia but without any radiotherapy, any radioisotope therapy and any antitumoral chemotherapy, in particular any antitumoral chemotherapy with an agent inducing DBS;

the use of a pharmaceutical composition comprising a) a conjugated Dbait molecule or hairpin nucleic acid molecule as disclosed herein, and b) an endosomolytic agent as described below for the manufacture of a medicament for the treatment of cancer in combination with hyperthermia;

the use of a pharmaceutical composition comprising a) a conjugated Dbait molecule or hairpin nucleic acid molecule as disclosed herein, and b) an endosomolytic agent as described below for the manufacture of a medicament for the treatment of cancer in combination with hyperthermia and with a radiotherapy, a radioisotope therapy and/or an antitumoral chemotherapy, preferably with a DNA-damaging anti-tumoral agent;

the use of a pharmaceutical composition comprising a) a conjugated Dbait molecule or hairpin nucleic acid molecule as disclosed herein, and b) an endosomolytic agent as described below for the manufacture of a medicament for the treatment of cancer in combination with hyperthermia but without any radiotherapy, any radioisotope therapy and any antitumoral chemotherapy, in particular any antitumoral chemotherapy with an agent inducing DBS;

the use of a pharmaceutical composition comprising a) a conjugated Dbait molecule or hairpin nucleic acid molecule as disclosed herein, and b) an endosomolytic agent as described below for the manufacture of a medicament for increasing the efficiency of the treatment of cancer with hyperthermia or for enhancing tumor sensitivity to hyperthermia;

the use of a pharmaceutical composition comprising a) a conjugated Dbait molecule or hairpin nucleic acid molecule as disclosed herein, and b) an endosomolytic agent as described below for the manufacture of a medicament for increasing the efficiency of the treatment of cancer with hyperthermia and radiotherapy, radioisotope therapy and/or an antitumoral chemotherapy, preferably with a DNA-damaging anti-tumoral agent; or for enhancing tumor sensitivity to hyperthermia combined with radiotherapy, radioisotope therapy and/or an antitumoral chemotherapy, preferably with a DNA-damaging anti-tumoral agent;

the use of a pharmaceutical composition comprising a) a conjugated Dbait molecule or hairpin nucleic acid molecule as disclosed herein, and b) an endosomolytic agent as described below for the manufacture of a medicament for increasing the efficiency of the treatment of cancer with hyperthermia without any radiotherapy, any radioisotope therapy and any antitumoral chemotherapy, in particular any antitumoral chemotherapy with an agent inducing DBS; or for enhancing tumor sensitivity to hyperthermia without any radiotherapy, any radioisotope therapy and any antitumoral chemotherapy, in particular any antitumoral chemotherapy with an agent inducing DBS;

the use of a pharmaceutical composition comprising a) a conjugated Dbait molecule or hairpin nucleic acid molecule as disclosed herein, b) an endosomolytic agent as described below, c) an antitumoral agent, preferably a DNA-damaging anti-tumoral agent, and d) a pharmaceutically acceptable carrier for the manufacture of a medicament for the treatment of cancer in combination with hyperthermia;

the use of a pharmaceutical composition comprising a) a conjugated Dbait molecule or hairpin nucleic acid molecule as disclosed herein, b) an endosomolytic agent as described below, c) an antitumoral agent, preferably a DNA-damaging anti-tumoral agent and d) a pharmaceutically acceptable carrier for the manufacture of a medicament for the treatment of cancer in combination with hyperthermia and with radiotherapy, radioisotope therapy and/or an antitumoral chemotherapy, preferably with a DNA-damaging anti-tumoral agent;

the use of a pharmaceutical composition comprising a) a conjugated Dbait molecule or hairpin nucleic acid molecule as disclosed herein, b) an endosomolytic agent as described below, c) an antitumoral agent, preferably a DNA-damaging anti-tumoral agent, and d) a pharmaceutically acceptable carrier for the manufacture of a medicament for the treatment of cancer in combination with hyperthermia but without any radiotherapy, any radioisotope therapy and any antitumoral chemotherapy, in particular any antitumoral chemotherapy with an agent inducing DBS;

a method for treating a cancer in a subject in need thereof, comprising i) administering an effective amount of a pharmaceutical composition comprising a Dbait molecule or hairpin nucleic acid molecule as disclosed herein, and a pharmaceutically acceptable carrier and, ii) subjecting the cancer cells of said subject to hyperthermia prior to, simultaneously with or subsequently to step i); thereby inducing cancer cells death;

a method for treating a cancer in a subject in need thereof, comprising i) administering a therapeutically effective amount of a pharmaceutical composition comprising a Dbait molecule or hairpin nucleic acid molecule as disclosed herein, and a pharmaceutically acceptable carrier and, ii) subjecting the cancer cells of said subject to hyperthermia prior to, simultaneously with or subsequently to step i); thereby inducing cancer cells death; optionally, the method further comprises administering to said subject a therapeutically effective amount of an antitumoral agent, preferably a DNA-damaging anti-tumoral agent or a radioisotopic agent; alternatively or in addition, the method further comprises subjecting the cancer cells of said subject to radiotherapy; alternatively, the method does not comprise the administration of any antitumoral drug, in particular of any agent inducing DBS, and a radioisotopic agent, and does not comprise subjecting the cancer cells of said subject to radiotherapy;

a method for treating a cancer in a subject in need thereof, comprising i) administering a therapeutically effective amount of a pharmaceutical composition comprising a) a conjugated Dbait molecule or hairpin nucleic acid molecule as disclosed herein, b) an endosomolytic agent as described below, and c) a pharmaceutically acceptable carrier; and ii) subjecting the cancer cells of said subject to hyperthermia prior to, simultaneously with or subsequently to step i); thereby inducing cancer cells death; optionally, the method further comprises administering to said subject a therapeutically effective amount of an antitumoral agent, preferably a DNA-damaging anti-tumoral agent or a radioisotopic agent; alternatively or in addition, the method further comprises subjecting the cancer cells of said subject to radiotherapy; alternatively, the method does not comprise the administration of any antitumoral drug, in particular of any agent inducing DBS, and a radioisotopic agent, and does not comprise subjecting the cancer cells of said subject to radiotherapy;

a method for increasing the efficiency of a treatment of a cancer with hyperthermia or for enhancing tumor sensitivity to hyperthermia in a subject in need thereof, comprising i) administering a therapeutically effective amount of a pharmaceutical composition comprising a) a conjugated Dbait molecule or hairpin nucleic acid molecule as disclosed herein, and b) a pharmaceutically acceptable carrier; and ii) subjecting the cancer cells of said subject to hyperthermia prior to, simultaneously with or subsequently to step i); thereby increasing cancer cells death; optionally, the method further comprises administering to said subject a therapeutically effective amount of an antitumoral agent, preferably a DNA-damaging anti-tumoral agent or a radioisotopic agent; alternatively or in addition, the method further comprises subjecting the cancer cells of said subject to radiotherapy; alternatively, the method does not comprise the administration of any antitumoral drug, in particular of any agent inducing DBS, and a radioisotopic agent, and does not comprise subjecting the cancer cells of said subject to radiotherapy;

a method for increasing the efficiency of a treatment of a cancer with hyperthermia or for enhancing tumor sensitivity to hyperthermia in a subject in need thereof, comprising i) administering a therapeutically effective amount of a pharmaceutical composition comprising a) a conjugated Dbait molecule or hairpin nucleic acid molecule as disclosed herein, b) an endosomolytic agent as described below, and c) a pharmaceutically acceptable carrier; and ii) subjecting the cancer cells of said subject to hyperthermia prior to, simultaneously with or subsequently to step i); thereby increasing cancer cells death; optionally, the method further comprises administering to said subject a therapeutically effective amount of an antitumoral agent, preferably a DNA-damaging anti-tumoral agent or a radioisotopic agent; alternatively or in addition, the method further comprises subjecting the cancer cells of said subject to radiotherapy; alternatively, the method does not comprise the administration of any antitumoral drug, in particular of any agent inducing DBS, and a radioisotopic agent, and does not comprise subjecting the cancer cells of said subject to radiotherapy.

The terms "kit", "product" or "combined preparation", as used herein, defines especially a "kit of parts" in the sense that the combination partners as defined above can be dosed independently or by use of different fixed combinations with distinguished amounts of the combination partners, i.e. simultaneously or at different time points. The parts of the kit of parts can then, e.g., be administered simultaneously or chronologically staggered, that is at different time points and with equal or different time intervals for any part of the kit of parts. The ratio of the total amounts of the combination partners to be administered in the combined preparation can be varied. The combination partners can be administered by the same route or by different routes.

Within the context of the invention, the term treatment denotes curative, symptomatic, and preventive treatment. Pharmaceutical compositions, kits, products and combined preparations of the invention can be used in humans with existing cancer or tumor, including at early or late stages of progression of the cancer. The pharmaceutical compositions, kits, products and combined preparations of the invention will not necessarily cure the patient who has the cancer but will delay or slow the progression or prevent further progression of the disease, ameliorating thereby the patients' condition. In particular, the pharmaceutical compositions, kits, products and combined preparations of the invention reduce the development of tumors, reduce tumor burden, produce tumor regression in a mammalian host and/or prevent metastasis occurrence and cancer relapse. In treating the cancer, the pharmaceutical composition of the invention is administered in a therapeutically effective amount.

By "therapeutically effective amount" it is meant the quantity of the pharmaceutical composition of the invention which prevents, removes or reduces the deleterious effects of cancer in mammals, including humans, alone or in combination with the other active ingredients of the pharmaceutical composition, kit, product or combined preparation. It is understood that the administered dose may be adapted by those skilled in the art according to the patient, the pathology, the mode of administration, etc.

Whenever within this whole specification "treatment of a cancer" or the like is mentioned with reference to the pharmaceutical composition of the invention, there is meant: a) a method for treating a cancer, said method comprising administering a pharmaceutical composition of the invention to a subject in need of such treatment; b) the use of a pharmaceutical composition of the invention for the treatment of a cancer; c) the use of a pharmaceutical composition of the invention for the manufacture of a medicament for the treatment of a cancer; and/or d) a pharmaceutical composition of the invention for use in the treatment a cancer.

The pharmaceutical compositions contemplated herein may include a pharmaceutically acceptable carrier in addition to the active ingredient(s). The term "pharmaceutically acceptable carrier" is meant to encompass any carrier (e.g., support, substance, solvent, etc.) which does not interfere with effectiveness of the biological activity of the active ingredient(s) and that is not toxic to the host to which it is administered. For example, for parental administration, the active compounds(s) may be formulated in a unit dosage form for injection in vehicles such as saline, dextrose solution, serum albumin and Ringer's solution.

The pharmaceutical composition can be formulated as solutions in pharmaceutically compatible solvents or as emulsions, suspensions or dispersions in suitable pharmaceutical solvents or vehicle, or as pills, tablets or capsules that contain solid vehicles in a way known in the art. Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. Formulations suitable for parental administration conveniently comprise a sterile oily or aqueous preparation of the active ingredient which is preferably isotonic with the blood of the recipient. Every such formulation can also contain other pharmaceutically compatible and nontoxic auxiliary agents, such as, e.g. stabilizers, antioxidants, binders, dyes, emulsifiers or flavouring substances. The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof. The pharmaceutical compositions are advantageously applied by injection or intravenous infusion of suitable sterile solutions or as oral dosage by the digestive tract. Methods for the safe and effective administration of most of these chemotherapeutic agents are known to those skilled in the art. In addition, their administration is described in the standard literature.

As used herein, the term "antitumoral chemotherapy" or "chemotherapy" refers to a cancer therapeutic treatment using chemical or biochemical substances, in particular using one or several antineoplastic agents. In particular, it also includes hormonal therapy and immunotherapy. The term "hormonal therapy" refers to a cancer treatment having for purpose to block, add or remove hormones. For instance, in breast cancer, the female hormones estrogen and progesterone can promote the growth of some breast cancer cells. So in these patients, hormone therapy is given to block estrogen and a non-exhaustive list commonly used drugs includes: Tamoxifen, Fareston, Arimidex, Aromasin, Femara, Zoladex/Lupron, Megace, and Halotestin. The term "immunotherapy" refers to a cancer therapeutic treatment using the immune system to reject cancer. The therapeutic treatment stimulates the patient's immune system to attack the malignant tumor cells.

Dbait Molecules

Dbait molecules have been extensively described in PCT patent applications WO2005/040378, WO2008/034866 and WO2008/084087, the disclosure of which is incorporated herein by reference.

Dbait molecules may be defined by a number of characteristics necessary for their therapeutic activity, such as their minimal length, the presence of at least one free end, and the presence of a double stranded portion, preferably a DNA double stranded portion. As will be discussed below, it is important to note that the precise nucleotide sequence of Dbait molecules does not impact on their activity. Furthermore, Dbait molecules may contain a modified and/or non-natural backbone.

Preferably, Dbait molecules are of non-human origin (i.e., their nucleotide sequence and/or conformation (e.g., hairpin) does not exist as such in a human cell), most preferably of synthetic origin. As the sequence of the Dbait molecules plays little, if any, role, Dbait molecules have preferably no significant degree of sequence homology or identity to known genes, promoters, enhancers, 5'- or 3'-upstream sequences, exons, introns, and the like. In other words, Dbait molecules have less than 80% or 70%, even less than 60% or 50% sequence identity to any gene in a human genome. Methods of determining sequence identity are well known in the art and include, e.g., Blast. Dbait molecules do not hybridize, under stringent conditions, with human genomic DNA. Typical stringent conditions are such that they allow the discrimination of fully complementary nucleic acids from partially complementary nucleic acids.

In addition, the sequence of the Dbait molecules is preferably devoid of CpG in order to avoid the well known toll-like receptor-mediated immunological reactions.

The length of Dbait molecules may be variable, as long as it is sufficient to allow appropriate binding of Ku protein complex comprising Ku and DNA-PKcs proteins. It has been showed that the length of Dbait molecules must be greater than 20 bp, preferably about 32 bp, to ensure binding to such a Ku complex and allowing DNA-PKcs activation. Preferably, Dbait molecules comprise between 20-200 bp, more preferably 24-100 bp, still more preferably 26-100, and most preferably between 24-200, 25-200, 26-200, 27-200, 28-200, 30-200, 32-200, 24-100, 25-100, 26-100, 27-100, 28-100, 30-100, 32-200 or 32-100 bp. For instance, Dbait molecules comprise between 24-160, 26-150, 28-140, 28-200, 30-120, 32-200 or 32-100 bp. By "bp" is intended that the molecule comprise a double stranded portion of the indicated length.

In a particular embodiment, the Dbait molecules having a double stranded portion of at least 32 pb, or of about 32 bp, comprise the same nucleotide sequence than Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5). Optionally, the Dbait molecules have the same nucleotide composition than Dbait32, Dbait32Ha, Dbait32Hb, Dbait32Hc or Dbait32Hd but their nucleotide sequence is different. Then, the Dbait molecules comprise one strand of the double stranded portion with 3 A, 6 C, 12 G and 11 T. Preferably, the sequence of the Dbait molecules does not contain any CpG dinucleotide.

Alternatively, the double stranded portion comprises at least 16, 18, 20, 22, 24, 26, 28, or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5). In a more particular embodiment, the double stranded portion consists in 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5).

Dbait must have at least one free end, as a mimic of DSB. Said free end may be either a free blunt end or a 5'-/3'-protruding end. The "free end" refers herein to a nucleic acid molecule, in particular a double-stranded nucleic acid portion, having both a 5' end and a 3' end or having either a 3' end or a 5' end. Optionally, one of the 5' and 3' end can be used to conjugate the Dbait molecule or can be linked to a blocking group, for instance a or 3'-3' nucleotide linkage.

In a particular embodiment, they contain two free ends and can be linear. Accordingly, Dbait molecules may also be a double stranded molecule with two free ends and having the nucleotide sequence of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5).

In another particular embodiment, they contain only one free end. Preferably, Dbait molecules are made of hairpin nucleic acids with a double-stranded DNA stem and a loop. The loop can be a nucleic acid, or other chemical groups known by skilled person or a mixture thereof. A nucleotide linker may include from 2 to 10 nucleotides, preferably, 3, 4 or 5 nucleotides. Non-nucleotide linkers non exhaustively include abasic nucleotide, polyether, polyamine, polyamide, peptide, carbohydrate, lipid, polyhydrocarbon, or other polymeric compounds (e.g. oligoethylene glycols such as those having between 2 and 10 ethylene glycol units, preferably 4, 5, 6, 7 or 8 ethylene glycol units). A preferred linker is selected from the group consisting of hexaethyleneglycol, tetradeoxythymidylate (T4) and other linkers such as 2,19-bis(phosphor)-8-hydraza-1-hydroxy-4-oxa-9-oxo-nonadecane. Accordingly, in a particular embodiment, the Dbait molecules can be a hairpin molecule having a double stranded portion or stem comprising at least 16, 18, 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5) and a loop being a hexaethyleneglycol linker, a tetradeoxythymidylate linker (T4) or 2,19-bis(phosphor)-8-hydraza-1-hydroxy-4-oxa-9-oxo-nonadecane. In a more particular embodiment, those Dbait molecules can have a double stranded portion consisting in 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5).

Dbait molecules preferably comprise a 2'-deoxynucleotide backbone, and optionally comprise one or several (2, 3, 4, 5 or 6) modified nucleotides and/or nucleobases other than adenine, cytosine, guanine and thymine. Accordingly, the Dbait molecules are essentially a DNA structure. In particular, the double-strand portion or stem of the Dbait molecules is made of deoxyribonucleotides.

Preferred Dbait molecules comprise one or several chemically modified nucleotide(s) or group(s) at the end of one or of each strand, in particular in order to protect them from degradation. In a particular preferred embodiment, the free end(s) of the Dbait molecules is(are) protected by one, two or three modified phosphodiester backbones at the end of one or of each strand. Preferred chemical groups, in particular the modified phosphodiester backbone, comprise phosphorothioates. Alternatively, preferred Dbait have 3'-3' nucleotide linkage, or nucleotides with methylphosphonate backbone. Other modified backbones are well known in the art and comprise phosphoramidates, morpholino nucleic acid, 2'-0, 4'-C methylene/ethylene bridged locked nucleic acid, peptide nucleic acid (PNA), and short chain alkyl, or cycloalkyl inter-sugar linkages or short chain heteroatomic or heterocyclic intrasugar linkages of variable length, or any modified nucleotides known by skilled person. In a first preferred embodiment, the Dbait molecules have the free end(s) protected by one, two or three modified phosphodiester backbones at the end of one or of each strand, more preferably by three modified phosphodiester backbones (in particular phosphorothioate or methylphosphonate) at least at the 3' end, but still more preferably at both 5' and 3' ends.

In a most preferred embodiment, the Dbait molecule is a hairpin nucleic acid molecule comprising a DNA double-stranded portion or stem of 32 bp (e.g., with a sequence selected from the group consisting of SEQ ID Nos 1-5, in particular SEQ ID No 4) and a loop linking the two strands of the DNA double-stranded portion or stem comprising or consisting of a linker selected from the group consisting of hexaethyleneglycol, tetradeoxythymidylate (T4) and 2,19-bis(phosphor)-8-hydraza-1-hydroxy-4-oxa-9-oxo-nonadecane, the free ends of the DNA double-stranded portion or stem (i.e. at the opposite of the loop) having three modified phosphodiester backbones (in particular phosphorothioate internucleotidic links).

Said Dbait molecules are made by chemical synthesis, semi-biosynthesis or biosynthesis, any method of amplification, followed by any extraction and preparation methods and any chemical modification. Linkers are provided so as to be incorporable by standard nucleic acid chemical synthesis.

More preferably, Dbait molecules are manufactured by specially designed convergent synthesis: two complementary strands are prepared by standard nucleic acid chemical synthesis with the incorporation of appropriate linker precursor, after their purification, they are covalently coupled together.

Optionally, the Dbait molecules may be conjugated to molecules facilitating endocytosis or cellular uptake.

In particular, the molecules facilitating endocytosis or cellular uptake may be lipophilic molecules such as cholesterol, single or double chain fatty acids, or ligands which target cell receptor enabling receptor mediated endocytosis, such as folic acid and folate derivatives or transferrin (Goldstein et al. Ann. Rev. Cell Biol. 1985 1:1-39; Leamon & Lowe, Proc Natl Acad Sci USA. 1991, 88: 5572-5576.). The molecule may also be tocopherol, sugar such as galactose and mannose and their oligosaccharide, peptide such as RGD and bombesin and protein such as integrin. Fatty acids may be saturated or unsaturated and be in $C_4$-$C_{28}$, preferably in $C_{14}$-$C_{22}$, still more preferably being in $C_{18}$ such as oleic acid or stearic acid. In particular, fatty acids may be octadecyl or dioleoyl. Fatty acids may be found as double chain form linked with in appropriate linker such as a glycerol, a phosphatidylcholine or ethanolamine and the like or linked together by the linkers used to attach on the Dbait molecule. As used herein, the term "folate" is meant to refer to folate and folate derivatives, including pteroic acid derivatives and analogs. The analogs and derivatives of folic acid suitable for use in the present invention include, but are not limited to, antifolates, dihydrofolates, tetrahydrofolates, folinic acid, pteropolyglutamic acid, 1-deza, 3-deaza, 5-deaza, 8-deaza, 10-deaza, 1,5-deaza, 5,10 dideaza, 8,10-dideaza, and 5,8-dideaza folates, antifolates, and pteroic acid derivatives. Additional folate analogs are described in US2004/242582. Accordingly, the molecule facilitating endocytosis may be selected from the group consisting of single or double chain fatty acids, folates and cholesterol. More preferably, the molecule facilitating endocytosis is selected from the group consisting of dioleoyl, octadecyl, folic acid, and cholesterol. In a most preferred embodiment, the Dbait molecule is conjugated to a cholesterol.

The molecules facilitating endocytosis are conjugated to Dbait molecules, preferably through a linker. Any linker known in the art may be used to covalently attach the molecule facilitating endocytosis to Dbait molecules For instance, WO09/126,933 provides a broad review of convenient linkers pages 38-45. The linker can be non-exhaustively, aliphatic chain, polyether, polyamine, polyamide, peptide, carbohydrate, lipid, polyhydrocarbon, or other polymeric compounds (e.g. oligoethylene glycols such as those having between 2 and 10 ethylene glycol units, preferably 3, 4, 5, 6, 7 or 8 ethylene glycol units, still more preferably 6 ethylene glycol units), as well as incorporating any bonds that may be break down by chemical or enzymatical way, such as a disulfide linkage, a protected disulfide linkage, an acid labile linkage (e.g., hydrazone linkage), an ester linkage, an ortho ester linkage, a phosphonamide linkage, a biocleavable peptide linkage, an azo linkage or an aldehyde linkage. Such cleavable linkers are detailed in WO2007/040469 pages 12-14, in WO2008/022309 pages 22-28.

In a particular embodiment, the Dbait molecule can be linked to one molecule facilitating endocytosis. Alternatively, several molecules facilitating endocytosis (e.g., two, three or four) can be attached to one Dbait molecule.

In a specific embodiment, the linker between the molecule facilitating endocytosis, in particular cholesterol, and Dbait molecule is $CO-NH-(CH_2-CH_2-O)_n$, wherein n is an integer from 1 to 10, preferably n being selected from the group consisting of 3, 4, 5 and 6. In a very particular embodiment, the linker is CO—NH—($C_2$—$CH_2$—O)$_4$ (carboxamido triethylene glycol). The linker can be linked to Dbait molecules at any convenient position which does not modify the activity of the Dbait molecules. In particular, the linker can be linked at the 5' end, at the 3' end or in the loop when the Dbait molecule is a hairpin. However, in the case of a hairpin Dbait molecule, the inventors surprisingly found that cholesterol linked to the Dbait molecule through a linker at its 5' end is more efficient than the cholesterol linked to the Dbait molecule through a linker at the loop. Therefore, in a preferred embodiment, the contemplated conjugated Dbait molecule is a Dbait molecule having a hairpin structure and being conjugated to the molecule facilitating endocytosis, preferably through a linker, at its 5' end.

In another specific embodiment, the linker between the molecule facilitating endocytosis, in particular cholesterol, and Dbait molecule is dialkyl-disulfide {e.g., $(CH_2)_r$—S—S—$(CH_2)_s$ with r and s being integer from 1 to 10, preferably from 3 to 8, for instance 6}.

In a most preferred embodiment, the conjugated Dbait molecule is a hairpin nucleic acid molecule comprising a DNA double-stranded portion or stem of 32 bp (e.g., with a sequence selected from the group consisting of SEQ ID Nos 1-5, in particular SEQ ID No 4) and a loop linking the two strands of the DNA double-stranded portion or stem comprising or consisting of a linker selected from the group consisting of hexaethyleneglycol, tetradeoxythymidylate (T4) and 2,19-bis(phosphor)-8-hydraza-1-hydroxy-4-oxa-9-oxo-nonadecane, the free ends of the DNA double-stranded portion or stem (i.e. at the opposite of the loop) having three modified phosphodiester backbones (in particular phosphorothioate internucleotidic links) and said Dbait molecule being conjugated to a cholesterol at its 5' end, preferably through a linker (e.g. carboxamido oligoethylene glycol, preferably carboxamido triethylene glycol).

The Dbait molecule or hairpin nucleic acid molecule, conjugated or not, can be also described by the following formulae:

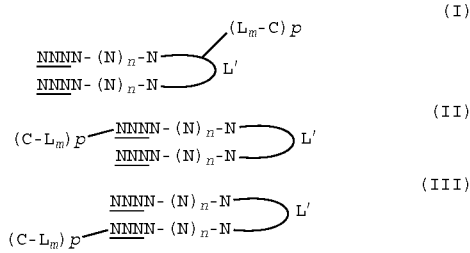

wherein N is a nucleotide, n is an integer greater than 14, the underlined N refers to a nucleotide having or not a modified phosphodiester backbone, L' is a linker, C is a molecule facilitating endocytosis, L is a linker, m and p, independently, are an integer being 0 or 1. In Formulae (II) and (III), C-$L_m$ is respectively linked to the 5' end or the 3' end of the nucleotide. In formula (I-III), C-$L_m$ is preferably linked to L' through a disulfide bond (S—S). When the molecule is conjugated, p is 1. Preferably, the underlined N refers to a nucleotide having a modified phosphodiester backbone.

In preferred embodiments, the molecule of formula (I), (II) or (III) has one or several of the following features:

N is a deoxynucleotide, preferably selected from the group consisting of A (adenine), C (cytosine), T (thymine) and G (guanine) and selected so as to avoid occurrence of a CpG dinucleotide and to have less than 80% or 70%, even less than 60% or 50% sequence identity to any gene in a human genome; and/or, n is an integer from 15 to 195, preferably from 19-95, more preferably from 21 to 95, and still more preferably from 27 to 95. In a particularly preferred embodiment, n is 27; and/or, the underlined N refers to a nucleotide having or not a phosphorothioate or methylphosphonate backbone, more preferably a phosphorothioate backbone; preferably, the underlined N refers to a nucleotide having a modified phosphodiester backbone; and/or, the linked L' is selected from the group consisting of hexaethyleneglycol, tetradeoxythymidylate (T4) and 2,19-bis(phosphor)-8-hydraza-1-hydroxy-4-oxa-9-oxo-nonadecane; and/or, m is 1 and L is a carboxamido polyethylene glycol, more preferably carboxamido triethylene glycol; and/or, C is selected from the group consisting of a cholesterol, single or double chain fatty acids such as octadecyl, oleic acid, dioleoyl or stearic acid, or ligand (including peptide, protein, aptamer) which targets cell receptor such as folic acid, tocopherol, sugar such as galactose and mannose and their oligosaccharide, peptide such as RGD and bombesin, and protein such transferring and integrin, preferably is a cholesterol;

Preferably, C-$L_m$ is a triethyleneglycol linker (10-O-[1-propyl-3-N-carbamoylcholesteryl]-triethyleneglycol radical.

In a preferred embodiment, the conjugated Dbait molecule or hairpin nucleic acid molecule has the following formula:

with the same definition than formulae (I), (II), (II') and (III) for N, N, n, L, L', C and m.

In a preferred embodiment, NNNN—(N)$_n$—N comprises at least 16, 18, 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5) or consists in 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5). In a particular embodiment, NNNN—(N)$_n$—N comprises or consists in Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5), more preferably Dbait32Hc (SEQ ID No 4).

According, the conjugated Dbait molecule or hairpin nucleic acid molecule may be selected from the group consisting of:

with NNNN-(N)$_n$-N being SEQ ID No 1

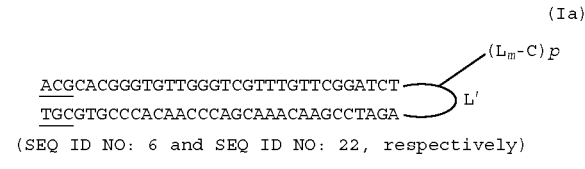

(SEQ ID NO: 6 and SEQ ID NO: 22, respectively)

(IIa)

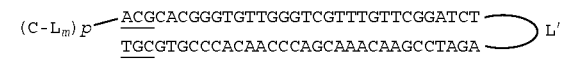

(SEQ ID NO: 11 and SEQ ID NO: 23, respectively);

(IIIa)

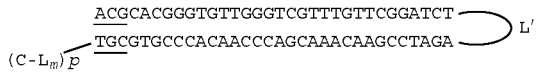

SEQ ID NO: 16 and SEQ ID NO: 24, respectively);

with NNNN-(N)$_n$-N being SEQ ID No 2

(Ib)

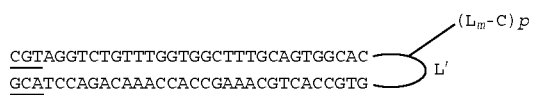

(SEQ ID NO: 7 and SEQ ID NO: 25, respectively);

(IIb)

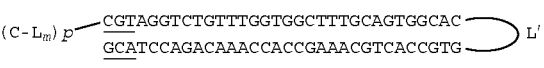

(SEQ ID NO: 12 and SEQ ID NO: 26, respectively);

(IIIb)

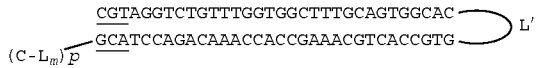

(SEQ ID NO: 17 and SEQ ID NO: 27, respectively);

with NNNN-(N)$_n$-N being SEQ ID No 3

(Ic)

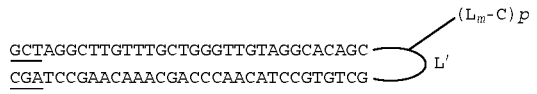

(SEQ ID NO: 8 and SEQ ID NO: 28, respectively);

(IIc)

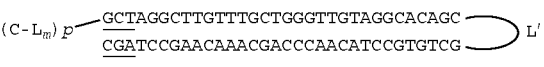

(SEQ ID NO: 13 and SEQ ID NO: 29, respectively);

(IIIc)

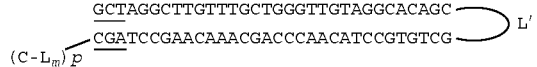

(SEQ ID NO: 18 and SEQ ID NO: 30, respectively);

with NNNN-(N)$_n$-N being SEQ ID No 4

(Id)

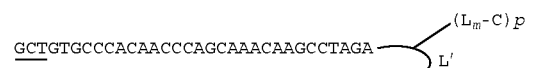

(SEQ ID NO: 9 and SEQ ID NO: 31, respectively);

(IId)

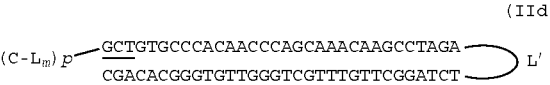

(SEQ ID NO: 14 and SEQ ID NO: 32, respectively);

(IIId)

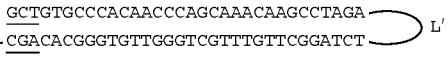

(SEQ ID NO: 19 and SEQ ID NO: 33, respectively);

with NNNN-(N)$_n$-N being SEQ ID No 5

(Ie)

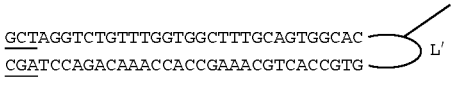

(SEQ ID NO: 10 and SEQ ID NO: 34, respectively);

(IIe)

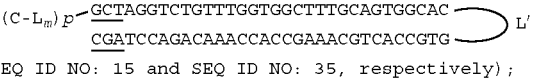

(SEQ ID NO: 15 and SEQ ID NO: 35, respectively);

and, (IIIe)

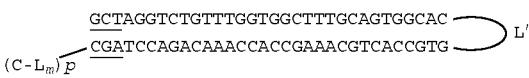

(SEQ ID NO: 20 and SEQ ID NO: 36, respectively);

with the same definition than formulae (I), (II) and (III) for L, L', C, p and m.

In preferred embodiments, the molecule of formulae (Ia), (IIa), (IIIa), (Ib), (IIb), (IIIb), (Ic), (IIc), (IIIc), (Id), (IId), (IIId), (Ie), (IIe) and (IIIe), preferably of formulae (II), (IIa), (IIb), (IIc), (IId) and (IIe), has one or several of the following features:
- the underlined nucleotide refers to a nucleotide having or not a phosphorothioate or methylphosphonate backbone, more preferably a phosphorothioate backbone; preferably, the underlined nucleotide refers to a nucleotide having a phosphorothioate or methylphosphonate backbone, more preferably a phosphorothioate backbone and/or,
- the linked L' is selected from the group consisting of hexaethyleneglycol, tetradeoxythymidylate (T4) and 2,19-bis(phosphor)-8-hydraza-1-hydroxy-4-oxa-9-oxo-nonadecane; and/or,
- m is 1 and L is a carboxamido polyethylene glycol, more preferably carboxamido triethylene glycol; and/or,
- p is 1; and/or,
- C is selected from the group consisting of a cholesterol, single or double chain fatty acids such as octadecyl, oleic acid, dioleoyl or stearic acid, or ligand (including peptide, protein, aptamer) which targets cell receptor such as folic acid, tocopherol, sugar such as galactose and mannose and their oligosaccharide, peptide such as RGD and bombesin, and protein such transferring and integrin, preferably is a cholesterol.

Preferably, C-Lm is a triethyleneglycol linker (10-O-[1-propyl-3-N-carbamoylcholesteryl]-triethyleneglycol radical.

In a specific embodiment of the Dbait molecules or hairpin nucleic acid molecules of formulae (I), (II), (II'), (III), (Ia), (IIa), (IIIa), (Ib), (IIb), (IIIb), (Ic), (IIc), (IIIc), (Id), (IId), (IIId), (Ie), (IIe) and (IIIe), preferably of formulae (II), (II'), (IIa), (IIb), (IIc), (IId) and (IIe), L' is preferably selected from the group consisting of hexaethyleneglycol, tetradeoxythymidylate (T4) and 2,19-bis(phosphor)-8-hydraza-1-hydroxy-4-oxa-9-oxo-nonadecane.

In a specific embodiment of the Dbait molecules or hairpin nucleic acid molecules of formulae (I), (II), (II'), (III), (Ia), (IIa), (IIIa), (Ib), (IIb), (IIIb), (Ic), (IIc), (IIIc), (Id), (IId), (IIId), (Ie), (IIe) and (IIIe), preferably of formulae (II), (II'), (IIa), (IIb), (IIc), (IId) and (IIe), with C being cholesterol, C-L$_m$ is the radical

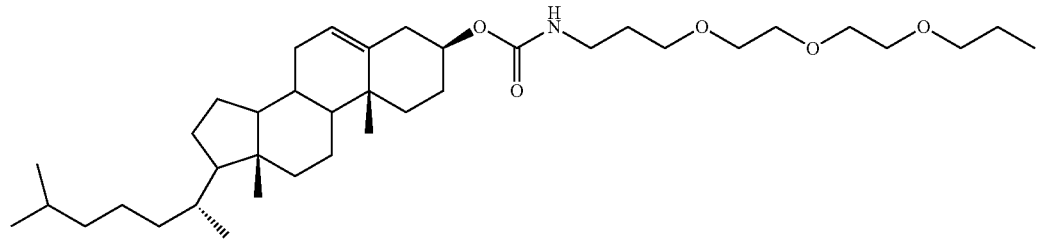 [SMILES: CCCOCCOCCOCCCNC(=O)O[C@H]1CC[C@@]2(C)C(=CCC3C4CCC([C@H](C)CCCC(C)C)[C@@]4(C)CCC32)C1]

In a preferred embodiment, the conjugated Dbait molecule or hairpin nucleic acid molecule is selected from the group consisting of (II), (II'), (IIa), (IIb), (IIc), (IId), and (IIe), wherein C-L$_m$ being the radical

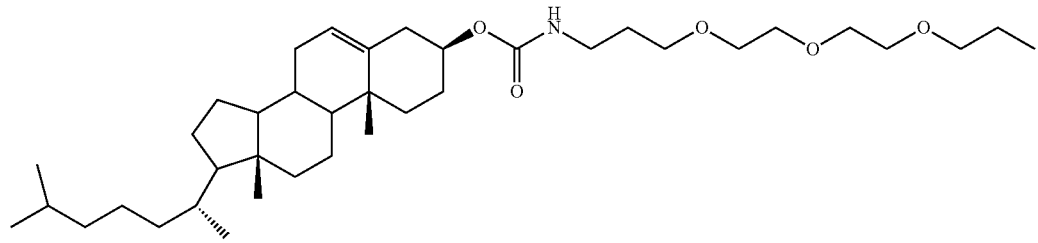 [SMILES: CCCOCCOCCOCCCNC(=O)O[C@H]1CC[C@@]2(C)C(=CCC3C4CCC([C@H](C)CCCC(C)C)[C@@]4(C)CCC32)C1]

and wherein L' is preferably selected from the group consisting of hexaethyleneglycol, tetradeoxythymidylate (T4) and 2,19-bis(phosphor)-8-hydraza-1-hydroxy-4-oxa-9-oxo-nonadecane, more preferably 2,19-bis(phosphor)-8-hydraza-1-hydroxy-4-oxa-9-oxo-nonadecane.

In a very specific embodiment, the Dbait molecule or hairpin nucleic acid molecule has the following formula wherein L' is 2,19-bis(phosphor)-8-hydraza-1-hydroxy-4-oxa-9-oxo-nonadecane and wherein the underlined nucleotides have a phosphorothioate backbone. Accordingly, the molecule has the following structure and it is referred thereto in the Example section as "coDbait" or "DT01".

(IId)

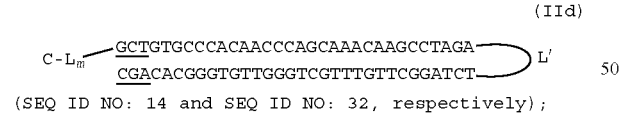

(SEQ ID NO: 14 and SEQ ID NO: 32, respectively);

wherein C-L$_m$ is the radical

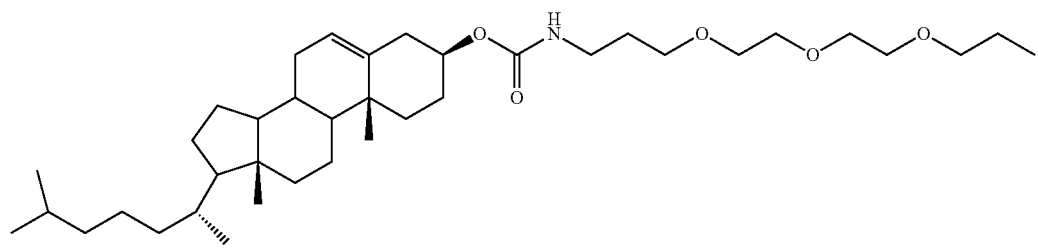 [SMILES: CCCOCCOCCOCCCNC(=O)O[C@H]1CC[C@@]2(C)C(=CCC3C4CCC([C@H](C)CCCC(C)C)[C@@]4(C)CCC32)C1]

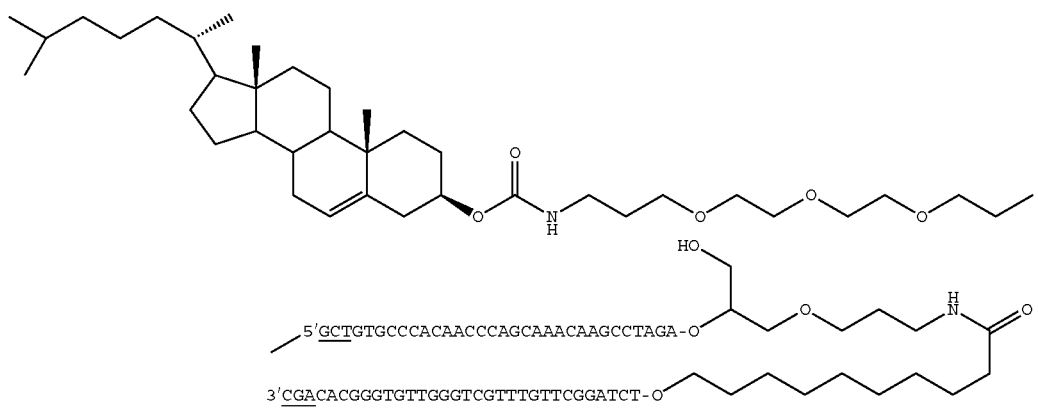

(SEQ ID NO: 21 and SEQ ID NO: 37, respectively).

Accordingly, the present invention also relates the use of a Dbait molecule as disclosed above, a pharmaceutical composition comprising it and optionally a pharmaceutically acceptable carrier, for use in the treatment of cancer in combination with hyperthermia, and with or without radiotherapy and/or radioisotope therapy and/or an antitumoral chemotherapy, preferably with a DNA damaging antitumoral agent, as detailed below.

Hyperthermia

Hyperthermia is a medical treatment in which body tissue is exposed to high temperatures to damage and kill cancer cells or to make cancer cells more sensitive to the effects of radiation and certain anti-cancer drugs. There are many techniques, well-known by the on skilled in the art, by which heat may be delivered.

Hyperthermia can be a local hyperthermia applied to the tumor, a regional hyperthermia applied to a tissue, an organ or a part thereof, or a whole-body hyperthermia. Hyperthermia treatment can be "acute" or "mild".

By "acute hyperthermia" is intended to refer to high temperatures between 50 and 100° C., preferably between 60 and 100° C. applied within the tumor to induce irreversible damage to mitochondrial and cytosolic enzymes of the cells in order to lead to thermal ablation of the tumor.

By "mild hyperthermia" is intended to refer to temperatures equal to that of a naturally high fever. A mild hyperthermia is a body temperature, and then the temperature of the cancer cells, of at least 40° C., preferably between 40 and 42° C., more preferably about 41° C. By "moderate hyperthermia" is intended to refer to methods heating the cancer cells at a temperature of at least 41° C., preferably in the range of 41-47° C., more preferably of 42-45° C. By "high hyperthermia" is intended to refer to methods heating the cancer cells at a temperature of at least 50° C. High hyperthermia is only applied as a local hyperthermia.

Hyperthermia may result from different methods well-known in the art. For instance, the hyperthermia treatment may be performed by microwaves (RFA), ultrasound (e.g., focused ultrasound (FUS or HIFU)), infrared rays, nanoparticles or nanotubes, induction heating, magnetic hyperthermia, perfusion or infusion of pre-warmed liquid such as blood, intraperitoneal heated flow, drug-induced hyperthermia, or direct application of heat.

Local hyperthermia consists of heating a very small area, preferably the tumor. In this context, the goal is to kill the tumor without other damages. The heat may be applied by microwave, radiofrequency, ultrasound energy or by using magnetic hyperthermia. The hyperthermia is, in this context, a moderate to high hyperthermia. Depending on the location of the tumor, the heat can be applied at the body surface (i.e., superficial hyperthermia), in a natural body cavity or deeper in the tissue through the use needles or probes (i.e., interstitial hyperthermia). In a preferred embodiment, hyperthermia is a radiofrequency ablation of the tumor.

Regional hyperthermia consists of heating a part of the body such an organ, a part thereof, a limb and the like. In this context, the hyperthermia is a moderate hyperthermia in order to preserve the organ or limb and to weaken the tumoral cells. Region hyperthermia can be performed by the same method than local hyperthermia with a decreased intensity or period. Alternatively, perfusion or infusion of pre-warmed liquid such as blood or intraperitoneal heated flow can be used. Optionally, when hyperthermia is combined with an antitumoral chemotherapy, the antitumoral agent may be added to the pre-warmed liquid. For instance, in order to treat peritoneal cancers, a continuous hyperthermic peritoneal perfusion (CHPP) may be used.

Whole-body hyperthermia is rather carried out in order to treat metastatic cancers. Direct application of heat can be carried out by sitting a patient in a hot room or wrapping him in hot blankets. Drug-induced hyperthermia refers to a method wherein a drug is administered to a subject in order to help a patient causes a fever. For instance, the drug may interfere with heat dissipation peripherally, increase the rate of metabolism, evoke a cellular or humoral immune response, mimic endogenous pyrogen, or damage tissues. In addition, whole-body hyperthermia may be carried out by the technique of infrared hyperthermia domes.

Endosomolytic Agent

Conjugated Dbait molecules or hairpin nucleic acid molecules are preferably used here in combination with an endosomolytic agent (ex. chloroquine, fusogenic lipids or peptides, etc.). Indeed, the treatment by an endosomolytic agent facilitates the release of conjugated Dbait molecules from endosomes. In particular, the endosomolytic agents are capable of effecting the lysis of the endosome in response to a change in pH, and an encapsulating, or packaging, component capable of packaging a therapeutic agent to be delivered to cellular or subcellular components. Endosomolytic substance that includes, but is not limited to, quinoline compounds, especially 4-aminoquinoline and 2-phenylquinoline compounds and amino, thio, phenyl, alkyl, vinyl and halogen derivatives thereof, fusogenic lipids, peptides or proteins.

In a preferred embodiment, the endosomolytic agent is a small molecule. The basic endosomolytic agent may be selected in the group consisting of quinine, chloroquine, hydroxychloroquines, amodiaquins (camoquines), amopyroquines, primaquines, mefloquines, nivaquines, halofantrines, quinone imines and a combination thereof. Preferred endosomolytic agents are quinoline endosomolytic agents including, but are not limited to, listed below compounds with their chemical name: 7-chloro-4-(4-diethylamino-1-methylbutylamino)quinoline (chloroquine); 7-chloro-4-(4-ethyl-(2-hydroxyethyl)-amino-1-methylbutylamino)quinoline (hydroxychloroquine); 7-fluoro-4-(4-diethylamino-1-methylbutylamino)quinoline; 4-(4-diethylamino-1-methylbutylamino) quinoline; 7-hydroxy-4-(4-diethylamino-1-methylbutylamino)quinoline; 7-chloro-4-(4-diethylamino-1-butylamino)quinoline (desmethylchloroquine); 7-fluoro-4-(4-diethylamino-1-butylamino)quinoline); 4-(4-diethylamino-1-butylamino) quinoline; 7-hydroxy-4-(4-diethylamino-1-butylamino) quinoline; 7-chloro-4-(1-carboxy-4-diethylamino-1-butylamino)quinoline; 7-fluoro-4-(1-carboxy-4-diethylamino-1-butylamino)quinoline; 4-(1-carboxy-4-diethylamino-1-butylamino)quinoline; 7-hydroxy-4-(1-carboxy-4-diethylamino-1-butylamino)quinoline; 7-chloro-4-(1-carboxy-4-diethylamino-1-methylbutylamino) quinoline; 7-fluoro-4-(1-carboxy-4-diethylamino-1-methylbutylamino)quinoline; 4-(1-carboxy-4-diethylamino-1-methylbutylamino)quinoline; 7-hydroxy-4-(1-carboxy-4-diethylamino-1-methylbutylamino)quinoline; 7-fluoro-4-(4-ethyl-(2-hydroxyethyl)-amino-1-methylbutylamino) quinoline; 4-(4-ethyl-(2-hydroxyethyl)-amino-1-methylbutylamino-)quinoline; 7-hydroxy-4-(4-ethyl-(2-hydroxyethyl)-amino-1-methylbutylamino) quinoline; hydroxychloroquine phosphate; 7-chloro-4-(4-ethyl-(2-hydroxyethyl-1)-amino-1-butylamino)quinoline (desmethylhydroxychloroquine); 7-fluoro-4-(4-ethyl-(2-hydroxyethyl)-amino-1-butylamino)quinoline; 4-(4-ethyl-(2-hydroxyethyl)-amino-1-butylamino)quinoline; 7-hydroxy-4-(4-ethyl-(2-hydroxyethyl)-amino-1-butylamino) quinoline; 7-chloro-4-(1-carboxy-4-ethyl-(2-hydroxyethyl)-amino-1-butylamino)quinoline; 7-fluoro-4-(1-carboxy-4-ethyl-(2-hydroxyethyl)-amino-1-butylamino)quinoline; 4-(1-carboxy-4-ethyl-(2-hydroxyethyl)-amino-1-butylamino)quinoline; 7-hydroxy-4-(1-carboxy-4-ethyl-(2-hydroxyethyl)-amino-1-butylamino)quinoline; 7-chloro-4-(1-carboxy-4-ethyl-(2-hydroxyethyl)-amino-1-methylbutylamino)quinoline; 7-fluoro-4-(1-carboxy-4-ethyl-(2-hydroxyethyl)-amino-1-methylbutylamino) quinoline; 4-(1-carboxy-4-ethyl-(2-hydroxyethyl)-amino-1-methylbutylamino)quinoline; 7-hydroxy-4-(1-carboxy-4-ethyl-(2-hydroxyethyl)-amino-1-methylbutylamino) quinoline; 8-[(4-aminopentyl)amino-6-methoxydihydrochloride quinoline; 1-acetyl-1,2,3,4-tetrahydroquinoline; 8-[(4-aminopentyl)amino]-6-methoxyquinoline dihydrochloride; 1-butyryl-1,2,3,4-tetrahydroquinoline; 3-chloro-4-(4-hydroxy-alpha, alpha'-bis(2-methyl-1-pyrrolidinyl)-2,5-xylidinoquinoline, 4-[(4-diethylamino)-1-methylbutyl-amino]-6-methoxyquinoline; 3-fluoro-4-(4-hydroxy-alpha, alpha'-bis(2-methyl-1-pyrrolidinyl)-2,5-xylidinoquinoline, 4-[(4-diethylamino)-1-methylbutyl-amino]-6-methoxyquinoline; 4-(4-hydroxy-alpha, alpha'-bis(2-methyl-1-pyrrolidinyl)-2,5-xylidinoquinoline; 4-[(4-diethylamino)-1-methylbutyl-amino]-6-methoxyquinoline; 3,4-dihydro-1-(2H)-quinolinecarboxyaldehyde; 1,1'-pentamethylene diquinoleinium diiodide; 8-quinolinol sulfate and amino, aldehyde, carboxylic, hydroxyl, halogen, keto, sulfhydryl and vinyl derivatives or analogs thereof.

Other agents are disclosed in Naisbitt et al (1997, *J Pharmacol Exp Therapy* 280:884-893) and in U.S. Pat. No. 5,736,557. In a more preferred embodiment, the endosomolytic agent may be selected from the group consisting of chloroquine, hydroxychloroquine, desmethylchloroquine, hydroxychloroquine phosphate, and desmethylhydroxychloroquine, preferably is chloroquine or hydroxychloroquine, more preferably chloroquine.

In another embodiment, the endosomolytic agent is a fusogenic lipid, peptide or protein. Indeed, numerous fusogenic lipids, peptides or proteins are known in the art. For instance, fusogenic lipids, peptides or proteins are those disclosed in the following patent applications: WO10057160, US2007/0293449, US2006/0051405, WO10053489, WO09126933. In particular, WO09/126,933 provides fusogenic lipids, peptides and proteins pages 23-29.

DNA Damaging Treatment

In addition to the Dbait molecules and hyperthermia, and endosomolytic agent when Dbait molecules are conjugated, the treatment may also further comprise an antitumoral treatment, preferably a treatment by a DNA damaging agent or radiotherapy.

The DNA-damaging treatment can be radiotherapy, or chemotherapy with a DNA-damaging antitumoral agent, or a combination thereof. DNA-damaging treatment refers to a treatment inducing DNA strand breakage, preferably relatively specifically in cancer cells.

DNA strand breakage can be achieved by ionized radiation (radiotherapy). Radiotherapy includes, but is not limited to, γ-rays, X-rays, and/or the directed delivery of radioisotopes to tumor cells. Other radiotherapies include microwaves and UV-irradiation. Other approaches to radiation therapy are also contemplated in the present invention.

DNA strand breakage can be achieved by radioisotope therapy, in particular by administration of a radioisotope, preferably a targeted radioisotope. Targeting can be due to the chemical properties of the isotope such as radioiodine which is specifically absorbed by the thyroid gland a thousand fold better than other organs. Alternatively, the targeting can be achieved by attaching to the radioisotope another molecule having targeting properties such hapten or antibody. Any of a number of suitable radioactive isotopes can be used, including, but not limited to, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-105, Palladium-109, Praseodymium-143, Promethium-149, Erbium-169, Iridium-194, Gold-198, Gold-199, and Lead-211.

The DNA-damaging antitumoral agent is preferably selected from the group consisting of an inhibitor of topoisomerases I or II, a DNA crosslinker, a DNA alkylating agent, an anti-metabolic agent and inhibitors of the mitotic spindles.

Inhibitors of topoisomerases I and/or II include, but are not limited to, etoposide, topotecan, camptothecin, irinotecan, amsacrine, intoplicine, anthracyclines such as doxorubicine, epirubicine, daunorubicine, idanrubicine and mitoxantrone. Inhibitors of Topoisomerase I and II include, but are not limited to, intoplecin.

DNA crosslinkers include, but are not limited to, cisplatin, carboplatin and oxaliplatin.

Anti-metabolic agents block the enzymes responsible for nucleic acid synthesis or become incorporated into DNA, which produces an incorrect genetic code and leads to apoptosis. Non-exhaustive examples thereof include, without limitation, folic acid antagonists, pyrimidine analogs, purine analogs and adenosine deaminase inhibitors, and more particularly Methotrexate, Floxuridine, Cytarabine, 6-Mercaptopurine, 6-Thioguanine, Fludarabine phosphate, Pentostatine, 5-fluorouracil, gemcitabine and capecitabine.

The DNA-damaging anti-tumoral agent can be alkylating agents including, without limitation, nitrogen mustards, ethylenimine derivatives, alkyl sulfonates, nitrosoureas, metal salts and triazenes. Non-exhaustive examples thereof include Uracil mustard, Chlormethine, Cyclophosphamide (CYTOXAN®), Ifosfamide, Melphalan, Chlorambucil, Pipobroman, Triethylenemelamine, Triethylenethiophosphoramine, Busulfan, Carmustine, Lomustine, Fotemustine, cisplatin, carboplatin, oxaliplatin, thiotepa, Streptozocin, Dacarbazine, and Temozolomide.

Inhibitors of the mitotic spindles include, but are not limited to, paclitaxel, docetaxel, vinorelbine, larotaxel (also called XRP9881; Sanofi-Aventis), XRP6258 (Sanofi-Aventis), BMS-184476 (Bristol-Meyer-Squibb), BMS-188797 (Bristol-Meyer-Squibb), BMS-275183 (Bristol-Meyer-Squibb), ortataxel (also called IDN 5109, BAY 59-8862 or SB-T-101131; Bristol-Meyer-Squibb), RPR 109881A (Bristol-Meyer-Squibb), RPR 116258 (Bristol-Meyer-Squibb), NBT-287 (TAPESTRY), PG-paclitaxel (also called CT-2103, PPX, paclitaxel poliglumex, paclitaxel polyglutamate or Xyotax™), ABRAXANE® (also called Nab-Paclitaxel; ABRAXIS BIOSCIENCE), Tesetaxel (also called DJ-927), IDN 5390 (INDENA), Taxoprexin (also called docosahexanoic acid-paclitaxel; PROTARGA), DHA-paclitaxel (also called Taxoprexin®), and MAC-321 (WYETH). Also see the review of Hennenfent & Govindan (2006, *Annals of Oncology*, 17, 735-749).

Cancers or Tumors to be Treated

The terms "cancer", "cancerous", or "malignant" refer to or describe the physiological condition in mammals that is typically characterized by unregulated cell growth. Examples of cancer include, for example, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), chronic lymphocytic leukemia, mastocytosis and any symptom associated with mastocytosis.

"Leukemia" refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia. In certain aspects, the present invention provides treatment for chronic myeloid leukemia, acute lymphoblastic leukemia, and/or Philadelphia chromosome positive acute lymphoblastic leukemia (Ph+ ALL).

Various cancers are also encompassed by the scope of the invention, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, retinoblastoma, gastric cancer, germ cell tumor, bone cancer, bone tumors, adult malignant fibrous histiocytoma of bone; childhood malignant fibrous histiocytoma of bone, sarcoma, pediatric sarcoma, sinonasal natural killer, neoplasms, plasma cell neoplasm; myelodysplastic syndromes; neuroblastoma; testicular germ cell tumor, intraocular melanoma, myelodysplastic syndromes; myelodysplastic/myeloproliferative diseases, synovial sarcoma. In addition, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, mast cell leukemia, in addition to other cancers. Other cancers are also included within the scope of disorders including, but are not limited to, the following: carcinoma, including that of the bladder, urothelial carcinoma, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma, and any metastasis thereof.

In a preferred embodiment of the present invention, the cancer is a solid tumor. The cancer may also be a blood cancer. For instance, the cancer may be sarcoma and oestosarcoma such as Kaposi sarcoma, AIDS-related Kaposi sarcoma, melanoma, in particular ulveal melanoma, and cancers of the head and neck, kidney, ovary, pancreas, prostate, thyroid, lung, esophagus, breast, bladder, colorectum, liver and biliary tract, uterine, appendix, and cervix, testicular cancer, gastrointestinal cancers and endometrial and peritoneal cancers. Preferably, the cancer may be sarcoma, melanoma, in particular ulveal melanoma, and cancers of the head and neck, kidney, ovary, pancreas, prostate, thyroid, lung, esophagus, breast, bladder, colorectum, liver, cervix, and endometrial and peritoneal cancers. In a very specific. embodiment, the cancer may be peritoneal and liver cancer. In a particular embodiment, the cancer may be large hepatic carcinoma and liver metastasis, in particular in combination with radiofrequency ablation (RFA). In another particular embodiment, the cancer may be peritoneal carcinomatisis, in particular in combination with hyperthermic peritoneal chemotherapy (HIPEC).

The pharmaceutical compositions and the products, kits or combined preparations described in the invention may be useful for inhibiting the growth of solid tumors, decreasing the tumor volume, preventing the metastatic spread of tumors and the growth or development of micrometastases. The pharmaceutical compositions and the products, kits or combined preparations described in the invention are in particular suitable for the treatment of poor prognosis patients or of radio- or chemo-resistant tumors.

Regimen, Dosages and Administration Routes

The effective dosage of each of the combination partners employed in the combined preparation of the invention may vary depending on the particular compound or pharmaceutical composition employed, the mode of administration, the condition being treated, the severity of the condition being treated. Thus, the dosage regimen of the combined preparation of the invention is selected in accordance with a variety of factors including the route of administration and the patient status. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites.

Hyperthermia treatment may be applied before to, simultaneously with or after the administration of Dbait molecules. More preferably, hyperthermia is applied after the administration of Dbait molecules preferably between 5 minutes and 24 hours, more preferably between 1 and 6 hours.

The administration route for Dbait molecules may be oral, parental, intravenous, intratumoral, subcutaneous, intracranial, intra-artery, topical, rectal, transdermal, intradermal, nasal, intramuscular, intraperitoneal, intraosseous, and the like. In a preferred embodiment, the Dbait molecules are to be administered or injected near the tumoral site(s) to be treated. In a particular embodiment, when the cancer to be treated is a peritoneal carcinomatosis, the Dbait molecules may be delivered with capnoperitoneum. In another particular embodiment, when the cancer to be treated is a hepatoma, the Dbait molecules may be delivered by intravenous, oral or intraarterial injection and embolisation. In a further particular embodiment, when the cancer to be treated is a melanoma, the Dbait molecules may be delivered by subcutaneous and intravenous injection. Another preferred administration route is an intra-tumoral injection.

When Dbait molecules are conjugated, the endosomolytic agent and the conjugated Dbait molecules may be administered by the same route or by two distinct routes. The administration route for the endosomolytic agent, preferably chloroquine or hydroxychloroquine, more preferably chloroquine, may be oral, parental, intravenous, intratumoral, subcutaneous, intracranial, intra-artery, topical, rectal, transdermal, intradermal, nasal, intramuscular, intraperitoneal, intraosseous, and the like. In a particular embodiment, the endosomolytic agent, preferably chloroquine or hydroxychloroquine, more preferably chloroquine, is to be administered by oral route or by intraperitoneal route, preferably by oral route. An advantage of the co-injection or local injection is that there is no need to match the pharmacokinetic profile in plasma.

In a first preferred embodiment with a conjugated Dbait molecule, the treatment regimen includes a step of pre-treatment of the patient with the endosomolytic agent, preferably chloroquine, before the beginning of the treatment with conjugated Dbait molecules or hairpin nucleic acid molecules. For instance, when the endosomolytic agent is administered near the tumoral site to be treated (e.g., local administration), it can be administered together or at least or about 1, 2, 3, 4 or 5 hours before the administration of conjugated Dbait molecules or hairpin nucleic acid molecules, preferably between about one to three hours before, more preferably about two hours before. Alternatively, when the endosomolytic agent is administered by systemic administration, it can be administered longer before the administration of conjugated Dbait molecules or hairpin nucleic acid molecules and by a longer treatment, preferably during a period of about one to three weeks before the administration of conjugated Dbait molecules or hairpin nucleic acid molecules, more preferably about a period of about two weeks. Once conjugated Dbait molecules or hairpin nucleic acid molecules are or have been administered, the treatment with the endosomolytic agent can continue as long as the cholesterol conjugated Dbait molecules or hairpin nucleic acid molecules are to be administered. Alternatively, the treatment with the endosomolytic agent can also end.

When a DNA-damaging antitumoral agent is used in combination with the Dbait molecule, the DNA-damaging antitumoral agent and the Dbait molecules may be administered by the same route or by distinct routes. The administration route for the DNA-damaging antitumoral agent may be oral, parenteral, intravenous, intratumoral, subcutaneous, intracranial, intraartery, topical, rectal, transdermal, intradermal, nasal, intramuscular, intraosseous, and the like.

In a particular embodiment, the DNA-damaging antitumoral agent is to be administered by oral route, and the Dbait molecules may be administered by intratumoral injection, by subcutaneous injection, by intraperitoneal injection, by intravenous injection, or by oral route, preferably by intratumoral, subcutaneous or intraperitoneal injection or by oral route, still more preferably by intratumoral or subcutaneous.

The Dbait molecules or hairpin nucleic acid molecules are to be administered before and/or simultaneously with and/or after the irradiation and/or the administration of the DNA-damaging antitumoral agent, more preferably before and/or simultaneously with the irradiation and/or the administration of the DNA-damaging antitumoral agent. The irradiation and/or the administration of the DNA-damaging antitumoral agent is performed so as the Dbait molecules are present in the tumoral cells when the irradiation is applied or when the DNA-damaging antitumoral agent reach the tumoral cells. The physician, clinician or veterinarian of ordinary skill can determine the regimen based on the active ingredients, their kinetics of availability to target sites or their pharmacokinetic profiles in plasma. Preliminary results indicate that Dbait molecules stay active during one day.

In a specific preferred embodiment with a conjugated Dbait molecule, the treatment regimen includes a step of pre-treatment of the patient with the endosomolytic agent, preferably chloroquine or hydroxychloroquine, more preferably chloroquine, before the beginning of the treatment with conjugated Dbait molecules or hairpin nucleic acid molecules. Then, the irradiation is to be applied or the DNA-damaging antitumoral agent is to be administered at the beginning of the treatment with conjugated Dbait molecules or hairpin nucleic acid molecules or after the treatment with conjugated Dbait molecules or hairpin nucleic acid molecules. For instance, the irradiation is to be applied or the DNA-damaging antitumoral agent is to be administered 3-24 h after the beginning of the treatment with conjugated Dbait molecules. The DNA-damaging antitumoral agent and conjugated Dbait molecules may also be simultaneously administered.

Once the treatment by radiotherapy or with the DNA-damaging antitumoral agent has begun, the treatment with the Dbait molecules can continue as long as the treatment by radiotherapy or with the DNA-damaging antitumoral agent is to be applied or administered. Alternatively, the treatment with the Dbait molecules can also end.

The effective dosage of the Dbait molecules employed in combination with hyperthermia may vary depending on the mode of administration, the condition being treated, the severity of the condition being treated. Thus, the dosage regimen of the Dbait molecules is selected in accordance with a variety of factors including the route of administration and the patient status. A physician, clinician or veterinarian of ordinary skill can readily determine and prescribe the effective amount of the Dbait molecules required to prevent, counter or arrest the progress of the cancer.

For instance, for local administration (e.g., when the intratumoral or sub-cutaneous administration is used), the efficient amount of the Dbait molecules is at least 0.01 mg per 1 $cm^3$ of tumor, preferably 0.1-40 mg per 1 $cm^3$ of tumor, most preferably 1-20 mg per 1 $cm^3$ of tumor. The efficient amount can be administered in a daily treatment protocol (e.g., 5 days per week for 3 to 6 consecutive weeks or 3 times a week for 3 to 6 consecutive weeks). Alternatively, an efficient amount of at least 0.1 mg per 1 $cm^3$ of tumor, preferably 0.1-40 mg per 1 $cm^3$ of tumor, most preferably 1-20 mg per 1 $cm^3$ of tumor, can be administered in a weekly treatment protocol for 3-6 consecutive weeks, for instance. When other administration routes are used, the one skilled in the art can adapt the amount in order to obtain an efficient amount of the Dbait molecules in the tumor of at least 0.01 mg per 1 $cm^3$ of tumor, preferably 0.1-40 mg per 1 $cm^3$ of tumor, most preferably 1-20 mg per 1 $cm^3$ of tumor, in particular in a daily treatment protocol or in a weekly treatment protocol. For instance, for a systemic route, the efficient amount or unit dosage of the Dbait molecules may be of 0.1 to 100 mg, preferably of 4 to 40 mg. Accordingly, for a systemic route, the efficient amount or unit dosage of the Dbait molecules may be of 0.06 to 0.6 mg/kg of patient. Of course, the dosage and the regimen can be adapted by the one skilled in art in consideration of the chemotherapy and/or radiotherapy regimen.

For the endosomolytic agent, in particular the chloroquine or hydroxychloroquine, more preferably chloroquine, the effective dosage of the endosomolytic agent employed in the combined preparation, kit or product of the invention may vary depending on the mode of administration, the condition being treated, the severity of the condition being treated. Thus, the dosage regimen of the endosomolytic agent is selected in accordance with a variety of factors including the route of administration and the patient status. A physician, clinician or veterinarian of ordinary skill can readily determine and prescribe the effective amount of the endosomolytic agent required to prevent, counter or arrest the progress of the cancer, in particular in combination with the conjugated Dbait molecules and the selected DNA damaging treatment. In a particular embodiment, when oral route is used and if the selected endosomolytic agent is known to be useful for treating or preventing malaria, the endosomolytic agent, in particular the chloroquine or hydroxychloroquine, more preferably chloroquine, is used with the same dose and regimen than for treating or preventing malaria. For instance, if the selected endosomolytic agent is chloroquine or hydroxychloroquine, more preferably chloroquine, chloroquine or hydroxychloroquine may be administered at 100-600 mg per day, preferably 200-400 mg per day, more preferably about 300 mg per day, once, twice, three times or four times a week. In a particular embodiment, chloroquine or hydroxychloroquine may be administered at about 100 mg per day during one or two weeks or at about 300 mg, twice a week during one or two weeks. In another particular embodiment, when local route is contemplated, for instance subcutaneous or intratumoral route, the endosomolytic agent, in particular the chloroquine or hydroxychloroquine, more preferably chloroquine, may be used with 100-300 mg.

For radiotherapy, any radiotherapy regimen known in the art may be used, in particular stereotactic irradiation (e.g., 15 Gy) or a fractionated irradiation. The use of a fractionated irradiation may be particularly efficient, for instance irradiation may be applied every day or every 2-5 days, preferably every 3-4 days, in a period of one, two, three, four, five or six weeks. The irradiation may be from 1 to 10 Gy, preferably from 2 to 5 Gy, in particular 2, 3, 4 or 5 Gy. For instance, fractionated irradiation of 15×2Gy in six weeks, or of 4 to 6×5Gy in two weeks may be contemplated. In a preferred embodiment, the contemplated radiotherapy is a protocol with 4 irradiations of 5 Gy in two weeks. Different regimens or conditions of combined treatments of cancer with irradiation and Dbait molecules have been tested and allowed to demonstrate the radio-sensitization of tumors by Dbait molecules depends on the doses of Dbait molecules but not of the irradiation doses.

For chemotherapy, the effective dosage of the DNA-damaging antitumoral agent employed in the combined preparation, kit or product of the invention or in combination with the composition of the invention may vary depending on the particular DNA-damaging antitumoral agent employed, the mode of administration, the condition being treated, the severity of the condition being treated. Thus, the dosage regimen of the DNA-damaging antitumoral agent is selected in accordance with a variety of factors including the route of administration and the patient status. A physician, clinician or veterinarian of ordinary skill can readily determine and prescribe the effective amount of the DNA-damaging antitumoral agent required to prevent, counter or arrest the progress of the cancer.

The treatment may include one or several cycles, for instance two to ten cycles, in particular two, three, four or five cycles. The cycles may be continued or separated. For instance, each cycle is separated by a period of time of one to eight weeks, preferably three to four weeks.

Further aspects and advantages of the present invention will be described in the following examples, which should be regarded as illustrative and not limiting.

EXAMPLES

Results

Dbait32Hc shows a synergic cytotoxicity when associated with hyperthermia in vitro First, the inventors tested MRC5 and HT29 cells treated with Dbait32Hc, or Dbait8H a transfection control with no activity on DNA-PK, then submitted during 1 h to hyperthermia at 43° C. and fixed 1 h later. To assess the relevance of a Dbait32Hc addition to RFA, the inventors have performed a trypan blue assay to measure treatment-induced cell death. After a Dbait32Hc treatment, MRC5 and HT29 cultures were submitted to hyperthermia, at 41 or 43° C. during 1 h, and cell death was evaluated 48 h later (FIG. 1). This assay has showed that, when cells were treated by a mild temperature shift, that cell death was not induced by itself. Addition of Dbait8H, inactive Dbait molecule did not change cell survival whereas addition of Dbait32Hc before temperature shift triggers 30% to 50% mortality. The effect was strictly dependent of DNA-PK since addition of NU7026 abolished the thermosensitization.

Histopathologic Analysis of Tumor Necrosis and Mitosis

HT29 flank xenografted mouse models were used to perform RFA, DT01 and combined treatments. In this study, DT01 intratumoral and subcutaneous injections were performed 24 and 5 hours before the RFA treatments. To evaluate the acute treatment efficacy, histological slices of large treated tumors were carried out 72 h after the treatments. Hematoxylin eosin staining was performed to analyse the tissue structure, the vascularization, the necrosis area, and the mitosis index (FIG. 3 and Table 1).

TABLE 1

| Treatment | Survival study | | | Pathological study | | | |
|---|---|---|---|---|---|---|---|
| | Median (days) | Partial response* | Complete response* | Number of samples | Mitosis** | Viable cells (%) | Tumoral area (mm$^2$) |
| Sham treated | 28 | 0/11 | 0/11 | 7 | 19.4 ± 1.5 | 74 ± 3 | 23.7 ± 8.2 |
| DT01 | 37 | 0/14 | 1/14 | 8 | 16 ± 1.3 | 54 ± 6.1 | 14.25 ± 1.5 |
| RFA | 40 | 1/13 | 1/13 | 8 | 14 ± 15 | 41 ± 6.4 | 13.5 ± 2.6 |
| RFA + DT01 | 57 | 3/11 | 6/11 | 8 | 4.4 ± 1.7 | 21 ± 6.6 | 5.75 ± 1.6 |

*RECIST criteria
**Mean value of 5 representative fields at magnification ×40 for each tumor sample.

Specimens treated with RFA (combined with DT01 or not) showed in the treatment zone, areas of coagulative necrosis, including atypical degenerative small cells with a hyperchromatic irregular nucleus, eosinophilic cytoplasm and a low mitotic rate (FIG. 3). The morphology of these dystrophic cells suggested a mechanism of necrobiosis compared to active, proliferating component. Specimens treated with RFA combined with DT01 (2 local injections of 6 mg each) showed significant larger areas of necrosis and degenerative dystrophic cells compared with RFA alone (p=0.03) or DT01 alone (p=0.0008), while untreated specimens showed little areas of spontaneous necrosis, especially for bigger tumors. Furthermore, for specimens treated with RFA combined with DT01, smaller areas of tumor that appeared to be viable were seen, mainly at the periphery (p<0.05), with smaller mitotic index (p<0.05). 3/8 specimens even showed no viable tumor at 72 h.

In conclusion, as shown in FIG. 3, specimens treated with RFA combined with DT01 showed significant larger areas of necrosis and degenerative cells, smaller areas of proliferative cells and lower number of mitosis compared with RFA alone or DT01 alone.

DT01 Enhances RFA Anti-Tumor Effect and Overall Survival

As shown in FIG. 2, treatment with either RFA or DT01 alone resulted in a moderate antitumor effect compared with no treatment. Combination therapy with RFA and DT01 resulted in synergistic reduction in tumor growth compared with treatment with RFA alone or DT01 alone.

With RFA and DT01, the combination therapy group had significantly enhanced survival compared with untreated animals, RFA alone and DT01 alone (FIG. 2C and Table 1). Mice treated by the combination DT01-RFA had significantly longer survival as compared to RFA alone (median survival: 57 vs 40 days, p<0.001) while RFA alone improved survival as compared to controls (median survival: 40 vs 28 days, p<0.001).

In order to evaluate the treatments' efficacy, treatments were performed on (large) xenografted tumors of homogenous sizes. DT01 local injections of 6 mg of molecules were performed once a day, during 4 consecutive days (24 mg in total respectively). The RFA treatments were performed 5 hours after the third injection of DT01. At days 1 and 4 after mock or RFA treatments, standardized pictures of the tumors were taken (FIG. 2A). Here, it was confirmed that DT01 alone induces tumor necrosis as compared to mock treatment. The RFA treatment alone triggered coagulation necrosis as showed by black necrosis area. However, when RFA was applied alone, the area of RFA-induced damage was limited and did not extend to the whole tumor volume. On the other hand, addition of DT01 to the RFA treatment allowed the coagulation necrosis to expand to the entire tumor volume.

In conclusion, as shown in FIG. 2, mice survival increased when animals received DT01 before RFA.

Materials and Methods

Cell Culture

MRC5 (human transformed fibroblast, ATCC (Manassas, Va.)) and HT29 (human colon adenocarcinoma, ATCC (Manassas, Va.)) cell lines were used for studies of cultured cells. The HT29 cell line was grown in complete DMEM (Gibco) supplemented with 10% fetal bovine serum (ATGC), streptomycin (100 mg·mL$^{-1}$, Invitrogen) and penicillin (100 mg·mL$^{-1}$, Invitrogen). Cells were maintained at 37° C. under a 5% $CO_2$ atmosphere, at 100% humidity.

Dbait Molecules

All Dbait molecules were synthesized by automated solid-phase oligonucleotide synthesis methods (Eurogentec). Note that for in vitro study, Dbait32Hc complexed with PEI was used whereas the cholesterol linked form DT01 was used in preclinical studies due to the high PEI toxicity on organism.

In Vitro Heat Shock Treatment and Trypan Blue Assays.

Cells were transfected by incubation with 2.5 µg of Dbait complexed with 11 kDa PEI (Poly +) in 800 µL of medium (in six-well plates) for 5 h. One nanomole of Dbait32Hc (molecular mass, 20,153) weighs ~20 µg. At the end of the Dbait transfection, transfection mediums were taken off and replaced by complete DMEM previously heat at 37° C. Immediately after, heat shock was performed in Fisher Scientific Isotemp at 43° C. during 1 hour. Then, cells were incubated under normal conditions during 48 hours. Cell supernatant and trypsinized pellet were mixed to count dead floating cells. Then the suspension was mixed with trypan blue to obtain a 0.4% trypan blue solution. Stained cells and total number of cells were counted on a Malassez chamber. The calculated percentage of unstained cells represents the percentage of viable cells.

Animal Model and (Tumor Preparation) Treatment

Six-week-old female NMRI nude mice were obtained from Janvier (Le Genest S$^r$ Isle, France). The animals were housed in the laboratory at least 1 week before starting experiments. There were 6 animals per cage under controlled conditions of light and dark cycles (12 h:12 h), relative humidity (55%), and temperature (21° C.). Food and tap water were available ad libitum. Human HT29 colon adenocarcinoma tumors were induced by injecting 80 mice subcutaneously with $10^7$ tumor cells in the right flank.

Preclinical Experimental Design

HT29 colon adenocarcinoma tumors were xenografted on 75 female adult nude mice. When tumor volumes reached 200 to 700 mm$^3$, (mean volume: 483±146 mm$^3$) mice were assigned to one of the treatment or control groups. Mice were treated with RFA alone, with Dbait via local injections alone, by combination of DT01 and RFA, or were untreated. 31 mice were sacrificed at day 3 for histopathological analysis, and 49 others were followed-up until sacrifice when tumors reached 2000 mm$^3$. In all experiments, tumors were measured with a digital caliper every 3 days. Tumor volumes were calculated in cubic millimeter using the following formula: length× width×width/2. The Local Committee on Ethics of Animal Experimentation approved all experiments.

Radiofrequency Tumor Ablation

RFA was performed using a Radionics Cool-tip RF (system radiofrequency) generator, under isoflurane anesthesia The RFA probe, consisting of a 15-gauge Cosman RF cannula electrode (Cosman Medical, inc, Burlington, USA), was inserted into the tumor. Power (in watts) was controlled manually until target temperature was reached. The ablation temperature was monitored by a subcutaneous thermocouple peripherally placed on the tumor. Peripheral temperature was maintained between 42 and 44° C. for 2 minutes (incomplete ablation scheme). When combined with Dbait, RFA was performed the third day of the treatment.

DT01 Treatment

Daily DT01 treatment was performed by one intratumoral injection (2 mg/animal) and two subcutaneous injections at opposite sites, 5 mm away from the tumor edge (2 mg/animal each).

Two protocol plans were used for consecutive daily DT01 treatment: a 2-day treatment for histopathological analysis and a 4-day treatment for survival study (total dose of 12 and 24 mg respectively). When combined with RFA, DT01 was administered 5 hours before ablation, on the second or the third day of DT01 treatment for the 2-day or the 4-day treatment respectively.

Histological Analysis

Three days after the RFA treatment, animals were sacrificed and tumors were excised. Tumors were fixed in neutral buffered formalin, embedded in paraffin. Seven µm sections were cut and stained with hematoxylin, eosin, safran (HES). The extent of necrosis (indicated by increased cell size, indistinct cell border, eosinophilic cytoplasm, loss or condensation of the nucleus, or associated inflammation) is expressed as the proportion (%) of the surface area of the tissue section analyzed that was necrotic. The number of mitotic cells and apoptotic cells were estimated from representative normecrotic fields of ~1,000 cells analyzed at high power.

Statistical Analysis

Statistical analyses were performed with StatEL software (ad Science). Overall survival curves were plotted from Kaplan-Meier estimates and compared. The nonparametric log-rank test was used for these comparisons because the data did not follow a normal distribution. Culture cell deaths were compared using a Student t-test.

The invention claimed is:

1. A method for treating a cancer in a subject in need thereof, the method comprising i) administering an effective amount of a pharmaceutical composition comprising a nucleic acid molecule having at least one free end and a DNA double stranded portion of 24-200 bp with less than 60% sequence identity to any gene in a human genome and a pharmaceutically acceptable carrier and, ii) subjecting the cancer cells of said subject to hyperthermia treatment prior to step i); thereby inducing cancer cell death.

2. The method according to claim 1, wherein the nucleic acid molecule has one of the following formulae:

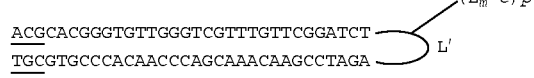

wherein N is a deoxynucleotide, n is an integer from 15 to 195, the underlined N refers to a nucleotide having or not a modified phosphodiester backbone, L' is a linker, C is the molecule facilitating endocytosis selected from a lipophilic molecule or a ligand which targets cell receptor enabling receptor mediated endocytosis, L is a linker, m and p, independently, are an integer being 0 or 1.

3. The method according to claim 1, wherein the nucleic acid molecule has one of the following formulae:

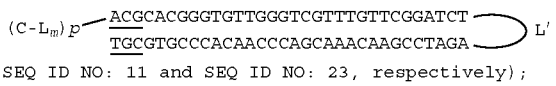

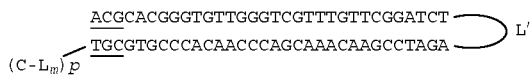

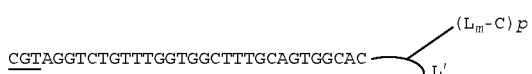

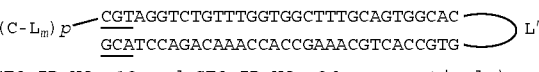

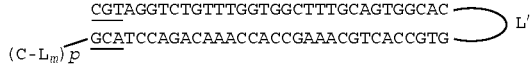

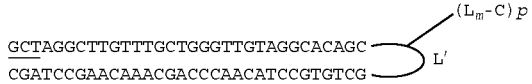

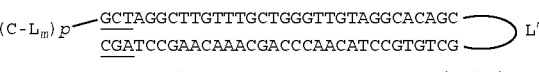

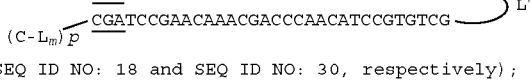

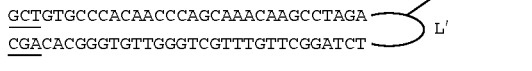

-continued (IId)

(C-L$_m$)$p$—GCTGTGCCCACAACCCAGCAAACAAGCCTAGA⏋L'
       CGACACGGGTGTTGGGTCGTTTGTTCGGATCT⏌

(SEQ ID NO: 14 and SEQ ID NO: 32, respectively);

(IIId)

GCTGTGCCCACAACCCAGCAAACAAGCCTAGA⏋L'
(C-L$_m$)$p$—CGACACGGGTGTTGGGTCGTTTGTTCGGATCT⏌

(SEQ ID NO: 19 and SEQ ID NO: 33, respectively);

(Ie)

GCTAGGTCTGTTTGGTGGCTTTGCAGTGGCAC⏋(L$_m$-C)$p$
CGATCCAGACAAACCACCGAAACGTCACCGTG⏌L'

(SEQ ID NO: 10 and SEQ ID NO: 34, respectively);

(IIe)

(C-L$_m$)$p$—GCTAGGTCTGTTTGGTGGCTTTGCAGTGGCAC⏋L'
       CGATCCAGACAAACCACCGAAACGTCACCGTG⏌

(SEQ ID NO: 15 and SEQ ID NO: 35, respectively);

and, (IIIe)

GCTAGGTCTGTTTGGTGGCTTTGCAGTGGCAC⏋L'
(C-L$_m$)$p$—CGATCCAGACAAACCACCGAAACGTCACCGTG⏌

(SEQ ID NO: 20 and SEQ ID NO: 36, respectively);

(Id)

GCTGTGCCCACAACCCAGCAAACAAGCCTAGA⏋(L$_m$-C)$p$
CGACACGGGTGTTGGGTCGTTTGTTCGGATCT⏌L'

(SEQ ID NO: 9 and SEQ ID NO: 31, respectively);

(IId)

(C-L$_m$)$p$—GCTGTGCCCACAACCCAGCAAACAAGCCTAGA⏋L'
       CGACACGGGTGTTGGGTCGTTTGTTCGGATCT⏌

(SEQ ID NO: 14 and SEQ ID NO: 32, respectively), and (IIId)

GCTGTGCCCACAACCCAGCAAACAAGCCTAGA⏋L'
(C-L$_m$)$p$—CGACACGGGTGTTGGGTCGTTTGTTCGGATCT⏌

(SEQ ID NO: 19 and SEQ ID NO: 33, respectively).

6. The method according to claim 1, wherein the nucleic acid molecule is

5'GCTGTGCCCACAACCCAGCAAACAAGCCTAGA-O
3'CGACACGGGTGTTGGGTCGTTTGTTCGGATCT-O (SEQ ID NO: 21 and SEQ ID NO: 37, respectively).

wherein the underlined nucleotide refers to a nucleotide having a phosphorothioate or methylphosphonate backbone, the linked L' is selected from the group consisting of hexaethyleneglycol, tetradeoxythymidylate (T4) and 2,19-bis(phosphor)-8-hydraza- 1-hydroxy-4-oxa-9-oxo-nonadecane; m is 1 and L is a carboxamido oligoethylene glycol, C is selected from the group consisting of single or double chain fatty acids, cholesterol, tocopherol, folic acid, sugar, a peptide and a protein.

4. The method according to claim 2, wherein the molecule facilitating endocytosis is cholesterol.

5. The method according to claim 1, wherein the nucleic acid molecule is selected from the group consisting of 7. The method according to claim 1, wherein the hyperthermia treatment involves a temperature of at least 41° C., or at least 42° C.

8. The method according to claim 1, wherein the hyperthermia treatment is performed by microwaves (RFA), ultrasound, infrared rays, nanoparticles or nanotubes, induction heating, magnetic hyperthermia, perfusion or infusion of pre-warmed liquid, intraperitoneal heated flow, or direct application of heat.

9. The method according to claim 1, wherein the cancer is a solid cancer.

10. The method according to claim 2, wherein p is 1 and the nucleic acid molecule is administered in combination with an endosomolytic agent.

11. The method according to claim 1, wherein the nucleic acid molecule is administered in combination with a radiotherapy and/or an antitumoral chemotherapy.

12. The method according to claim 11, wherein the antitumoral chemotherapy is a treatment by a DNA damaging antitumoral agent, either directly or indirectly.

13. The method according to claim 12, wherein the DNA damaging antitumoral agent is selected from the group consisting of an inhibitor of topoisomerases I or II, a DNA crosslinker, a DNA alkylating agent, an anti-metabolic agent and inhibitors of the mitotic spindles.

14. The method according to claim 1, wherein the nucleic acid molecule is not administered in combination with a radiotherapy and/or an antitumoral chemotherapy.

15. The method according to claim 1, wherein the nucleic acid molecule is not administered in combination with a radiotherapy and/or an antitumoral chemotherapy with a DNA damaging antitumoral agent.

16. The method according to claim 9, wherein said solid cancer is selected from sarcoma, melanoma, and cancers of the head and neck, cancers of the kidney, cancers of the ovary, cancers of the pancreas, cancers of the prostate, cancers of the thyroid, cancers of the lung, cancers of the esophagus, cancers of the breast, cancers of the bladder, cancers of the colorectum, cancers of the liver, cancers of the cervix, endometrial cancers and peritoneal cancers.

17. The method according to claim 1, wherein the hyperthermia treatment comprises heating cancer cells to a temperature of at least 50° C.

18. The method according to claim 1, wherein the hyperthermia treatment comprises heating cancer cells to a temperature of 42° C. to 45° C.

19. The method according to claim 1, wherein the hyperthermia treatment comprises heating cancer cells to a temperature of at least 45° C. to 47° C.

20. A method for treating a cancer in a subject in need thereof, the method comprising i) administering an effective amount of a pharmaceutical composition comprising a nucleic acid molecule having at least one free end and a DNA double stranded portion of 24-200 bp with less than 60% sequence identity to any gene in a human genome and a pharmaceutically acceptable carrier and, ii) subjecting the cancer cells of said subject to hyperthermia treatment prior to, or simultaneously with step i); thereby inducing cancer cell death.

* * * * *